United States Patent
Bonaventure et al.

(10) Patent No.: US 8,883,808 B2
(45) Date of Patent: Nov. 11, 2014

(54) COMBINATION OF 5-HT7 RECEPTOR ANTAGONIST AND SEROTONIN REUPTAKE INHIBITOR THERAPY

(75) Inventors: Pascal Bonaventure, San Diego, CA (US); Christine Dugovic, San Diego, CA (US); Curt A. Dvorak, San Diego, CA (US); Dale A. Rudolph, San Diego, CA (US); Jonathan Edward Shelton, San Diego, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 1168 days.

(21) Appl. No.: 12/375,393

(22) PCT Filed: Oct. 18, 2006

(86) PCT No.: PCT/US2006/040911
§ 371 (c)(1),
(2), (4) Date: Jan. 27, 2009

(87) PCT Pub. No.: WO2008/013556
PCT Pub. Date: Jan. 31, 2008

(65) Prior Publication Data
US 2009/0275563 A1 Nov. 5, 2009

Related U.S. Application Data

(63) Continuation-in-part of application No. 11/460,294, filed on Jul. 27, 2006, now Pat. No. 7,598,255.

(60) Provisional application No. 60/705,719, filed on Aug. 4, 2005.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC .................. 514/266.1; 544/283; 544/284

(58) Field of Classification Search
USPC .................... 514/266.1; 544/283, 284
See application file for complete search history.

(56) References Cited

U.S. PATENT DOCUMENTS

| | | |
|---|---|---|
| 3,248,395 A | 4/1966 | Ohnacker et al. |
| 3,312,716 A | 4/1967 | Biel et al. |
| 3,969,355 A | 7/1976 | Schwan |
| 4,007,196 A | 2/1977 | Christensen et al. |
| 4,136,193 A | 1/1979 | Bogeso et al. |
| 4,314,081 A | 2/1982 | Molloy et al. |
| 4,536,518 A | 8/1985 | Welch, Jr. et al. |
| 4,576,604 A | 3/1986 | Guittard et al. |
| 4,614,149 A | 9/1986 | Omi |
| 4,673,405 A | 6/1987 | Guittard et al. |
| 4,857,330 A | 8/1989 | Stephens et al. |
| 5,137,890 A | 8/1992 | Sanfilippo et al. |
| 5,405,848 A | 4/1995 | Sanfilippo et al. |
| 5,997,905 A | 12/1999 | McTeigue et al. |
| 6,025,367 A | 2/2000 | Forbes et al. |
| 6,149,943 A | 11/2000 | McTeigue et al. |
| 6,355,642 B1 | 3/2002 | Koyama et al. |
| 6,407,112 B1 | 6/2002 | Koyama et al. |
| 6,414,149 B1 | 7/2002 | Chu-Moyer et al. |
| 7,598,255 B2 | 10/2009 | Dvorak |
| 2002/0183519 A1 | 12/2002 | Nar et al. |
| 2003/0153728 A1 | 8/2003 | Kolb et al. |
| 2004/0229874 A1 | 11/2004 | Bright et al. |
| 2005/0119295 A1 | 6/2005 | Carruthers et al. |
| 2005/0232986 A1 | 10/2005 | Brown et al. |
| 2005/0288355 A1 | 12/2005 | Mork et al. |
| 2006/0194837 A1 | 8/2006 | Carruthers et al. |
| 2006/0287292 A1 | 12/2006 | Carruthers et al. |
| 2006/0293316 A1 | 12/2006 | Apodaca et al. |
| 2007/0032481 A1 | 2/2007 | Dvorak et al. |
| 2007/0260057 A1 | 11/2007 | Deng et al. |
| 2008/0004258 A1 | 1/2008 | Keith et al. |
| 2008/0045508 A1 | 2/2008 | Allison et al. |
| 2008/0045509 A1 | 2/2008 | Allison et al. |
| 2008/0139564 A1 | 6/2008 | Keith et al. |
| 2009/0275563 A1 | 11/2009 | Bonaventure |

FOREIGN PATENT DOCUMENTS

| | | |
|---|---|---|
| EP | 937715 A1 | 8/1999 |
| EP | 0 958 824 A2 | 11/1999 |
| EP | 1264820 A1 | 12/2002 |
| EP | 1211246 B1 | 2/2004 |
| EP | 937715 B1 | 6/2005 |
| JP | 03 148265 A | 6/1991 |
| JP | 2002 541109 A | 12/2002 |
| JP | 2004 529905 T | 9/2004 |
| WO | 95/29909 A1 | 11/1995 |
| WO | WO 95/29909 A1 | 11/1995 |
| WO | 96/32944 A1 | 10/1996 |
| WO | WO 96/32944 A1 | 10/1996 |
| WO | 97/29097 A1 | 8/1997 |
| WO | WO 97/29097 A1 | 8/1997 |
| WO | 97/47601 A1 | 12/1997 |
| WO | 97/48681 A1 | 12/1997 |
| WO | 97/49695 A1 | 12/1997 |
| WO | WO 97/47601 A1 | 12/1997 |
| WO | WO 97/48681 A1 | 12/1997 |

(Continued)

OTHER PUBLICATIONS

Extended European Search Report for Corresponding EP Application No. 06817172.7 dated Jun. 6, 2011.

(Continued)

*Primary Examiner* — Paul V. Ward
(74) *Attorney, Agent, or Firm* — Michael J. Atkins

(57) ABSTRACT

Patients suffering from serotonin-mediated diseases or conditions, such as depression, may be treated by administering an effective combined amount of a 5-HT7 receptor antagonist and a serotonin reuptake inhibitor.

15 Claims, 17 Drawing Sheets

(56) References Cited

FOREIGN PATENT DOCUMENTS

| WO | WO 97/49695 A1 | 12/1997 |
| WO | 98/00400 A1 | 1/1998 |
| WO | WO 98/00400 A1 | 1/1998 |
| WO | 98/31354 A3 | 7/1998 |
| WO | WO 98/31354 A3 | 7/1998 |
| WO | 99 22804 A1 | 5/1999 |
| WO | 99/24022 A3 | 5/1999 |
| WO | WO 99 22804 A1 | 5/1999 |
| WO | WO 99/24022 A3 | 5/1999 |
| WO | 99 54303 A1 | 10/1999 |
| WO | WO 99 54303 A1 | 10/1999 |
| WO | WO 00 24399 A1 | 5/2000 |
| WO | 00/32173 A1 | 6/2000 |
| WO | 00/37082 A1 | 6/2000 |
| WO | WO 00/32173 A1 | 6/2000 |
| WO | WO 00/37082 A1 | 6/2000 |
| WO | 00/56712 A1 | 9/2000 |
| WO | WO 00/56712 A1 | 9/2000 |
| WO | 00/59510 A1 | 10/2000 |
| WO | WO 00/59510 A1 | 10/2000 |
| WO | 00/73299 A1 | 12/2000 |
| WO | WO 00/73299 A1 | 12/2000 |
| WO | 01/29029 A1 | 4/2001 |
| WO | WO 01/29029 A1 | 4/2001 |
| WO | 01/41766 A1 | 6/2001 |
| WO | WO 01/41766 A1 | 6/2001 |
| WO | 01/57039 A1 | 8/2001 |
| WO | WO 01/57039 A1 | 8/2001 |
| WO | 02/014314 A2 | 2/2002 |
| WO | WO 02/14314 A2 | 2/2002 |
| WO | 02/062788 A1 | 8/2002 |
| WO | WO 02/062788 A1 | 8/2002 |
| WO | WO 02 062788 A1 | 8/2002 |
| WO | WO 02 072558 A1 | 9/2002 |
| WO | 03/035070 A1 | 5/2003 |
| WO | WO 03/035070 A1 | 5/2003 |
| WO | 03/053330 A2 | 7/2003 |
| WO | WO 03/053330 A2 | 7/2003 |
| WO | 2004/011467 A1 | 2/2004 |
| WO | WO 2004/011467 A1 | 2/2004 |
| WO | 2004 039786 A1 | 5/2004 |
| WO | WO 2004 037190 A2 | 5/2004 |
| WO | WO 2004 039786 A1 | 5/2004 |
| WO | 2004 094419 A1 | 11/2004 |
| WO | WO 2004 094419 A1 | 11/2004 |
| WO | 2005 005387 A1 | 1/2005 |
| WO | WO 2005 005387 A1 | 1/2005 |
| WO | 2005 030132 A2 | 4/2005 |
| WO | WO 2005 030132 A2 | 4/2005 |
| WO | 2005 040169 A2 | 5/2005 |
| WO | WO 2005 040169 A2 | 5/2005 |
| WO | 2005 056056 A2 | 6/2005 |
| WO | WO 2005 056056 A2 | 6/2005 |
| WO | 2006 016262 A1 | 2/2006 |
| WO | WO 2006 016262 A1 | 2/2006 |
| WO | 2006 023552 A1 | 3/2006 |
| WO | WO 2006 023552 A1 | 3/2006 |
| WO | 2006 066197 A1 | 6/2006 |
| WO | WO 2006 066197 A1 | 6/2006 |
| WO | WO 2007 019083 A1 | 2/2007 |
| WO | WO 2007 106349 A2 | 9/2007 |
| WO | 2008/013556 A1 | 1/2008 |
| WO | WO 2008/013556 A1 | 1/2008 |

OTHER PUBLICATIONS

Yamanaka et al "Studies on Pyrimidine Derivatives XVIII. Reaction of Active Methyl Groups on Pyrimidine N-Oxides" Chemical & Pharmaceutical Bulletin 1980 vol. 28(5) pp. 1526-1533.

Herrera et al "A Facile Synthesis of New Tetrahydropyrido[4,3-D]Pyrimidine Derivatives" Tetrahedron Letters 2006 vol. 47(31) pp. 5463-5465.

TIPO'S Search Report for Corresponding ROC Application No. 095128407 dated Mar. 6, 2012.

Slassi et al "Recent Progress in 5-HT7 Receptors: Potential Treatment of Central and Peripheral Nervous System Diseases" Expert Opinion on Therapeutic Patents 2004 vol. 14(7) pp. 1009-1027.

U.S. Appl. No. 60/326,662, Kanamarlapudi et al., filed Oct. 2, 2001.

U.S. Appl. No. 60/746,497, Deng et al., filed May 5, 2006.

U.S. Appl. No. 60/806,169, Allison et al., filed Jun. 29, 2006.

U.S. Appl. No. 60/806,167, Allison et al., filed Jun. 29, 2006.

U.S. Appl. No. 60/806,165, Keith et al., filed Jun. 29, 2006.

U.S. Appl. No. 60/938,790, Keith, filed May 18, 2007.

Appell, M. et al. An analysis of the binding of cocaine analogues to the monamine transporters using tensor decomposition 3-D QSAR. Bioorg. Med. Chem. 2002, 10(5), 1197-1206.

Bard et al. Cloning of a Novel Human Serotonin Receptor (5-HT$_7$) Positively Linked to Adenylate Cyclase. J. Biol. Chem. 1993, 268(31), 23422-23426.

Bonaventure, P. et al. Radioligand Binding Analysis of Knockout Mice Reveals 5-Hydroxytryptamine$_7$ Receptor Distribution and Uncovers 5-Hydroxy-2-(di-N-propylamino)tetralin Interaction with $\alpha_2$ Adrenergic Receptors. Neuroscience 2004, 124, 901-911.

Guscott et al. The hypothermic effect of 5-CT in mice is mediated through the 5-HT$_7$ receptor. Neuropharmacology 2003, 44(8), 1031-1037.

Harsing et al. A 5-HT$_7$ Heteroreceptor-Mediated Inhibition of [$^3$H]Serotonin Release in Raphe Nuclei Slices of the Rat: Evidence for a Serotonergic-Glutamatergic Interaction. Neurochem. Res. 2004, 29(8), 1487-1497.

Hedlund et al. No hypothermic response to serotonin in 5-HT$_7$ receptor knockout mice. Proc. Natl. Acad. Sci. U.S.A. 2003, 100(3), 1375-1380.

Hoyer, D. et al. Molecular, pharmacological and functional diversity of 5-HT receptors. Pharmacol. Biochem. Behav. 2002, 71, 533-554.

Kim et al "Mutation Screening of Human 5-HT28 Receptor Gene in Early-Onset Obsessive-Compulsive Disorder" Molec & Cellular Probes 2000 vol. 14 pp. 47-52.

Murphy et al. Experimental gene interaction studies with SERT mutant mice as models for human polygenic and epistatic traits and disorders. Genes, Brain & Behav. 2003, 2(6), 350-364.

Silvestre et al "Research on adverse drug events. I. Muscarinic M3 receptor binding affinity could predict the risk of antipsychotics to induce type 2 diabetes" Methods Find Exp Clin Pharrnacol 2005 vol. 27(5) pp. 289-304.

Simons et al. The Pharmacology and Use of H$_1$-Receptor-Antagonist Drugs. N. Engl. J. Med. 1994, 330, 1663-1670.

Tagawa et al. Neuroimaging of histamine H$_1$-receptor occupancy in human brain by positron emission tomography (PET): A comparative study of ebastine, a second-generation antihistamine, and (+)-chlorpheniramine, a classical antihistamine. Br. J. Clin. Pharmacol. 2001, 52(5), 501-509.

Tashiro et al. Brain histamine H$_1$ receptor occupancy of orally administered antihistamines measured by positron emission tomography with $^{11}$C-doxepin in a placebocontrolled crossover study design in healthy subjects: a comparison of olopatadine and ketotifen. Br. J. Clin. Pharmacol. 2006, 61(1), 16-26.

Tashiro et al. Central Effects of Fexofenadine and Cetirizine: Measurement of Psychomotor Performance, Subjective Sleepiness, and Brain Histamine H$_1$-Receptor Occupancy Using $^{11}$C-Doxepin Positron Emission Tomography. J. Clin. Pharmacol. 2004, 44(8), 890-900.

Thomas et al. SB-656104-A, a novel selective 5-HT$_7$ receptor antagonist, modulates REM sleep in rats. Br. J. Pharmacol. 2003, 139(4), 705-714.

Thomas et al. [$^3$H]-SB-269970 radiolabels 5-HT$_7$ receptors in rodent, pig and primate brain tissues. Neuropharmacology 2002, 42(1), 74-81.

Thomas et al. 5-HT$_7$ Receptors. Curr. Drug Targets CNS Neurol. Disord. 2004, 3(1), 81-90.

To et al. Characterization and distribution of putative 5-HT$_7$ receptors in guinea-pig brain. Br. J. Pharmacol. 1995, 115(1), 107-116.

Tuladhar et al. 5-HT$_7$ receptors mediate the inhibitory effect of 5-HT on peristalsis in the isolated guinea-pig ileum. Br. J. Pharmacol. 2003, 138(7), 1210-1214.

Vanhoenacker et al. 5-HT$_7$ receptors: current knowledge and future prospects. Trends Pharmacol. Sci. 2000, 21, 70-77.

(56) References Cited

OTHER PUBLICATIONS

Varnas et al. Distribution of 5-HT$_7$ receptors in the human brain: a preliminary autoradiographic study using [$^3$H]SB-269970. Neurosci. Lett. 2004, 367(3), 313-316.
Welch et al. H$_1$-Antihistamines and the central nervous system. In *Histamine and H$_1$ Antihistamines in Allergic Disease*, 2$^{nd}$ ed.; F.E.R. Simons, Ed.; Marcel Dekker, Inc.: New York, 2002; Chapter 11.
Yanai et al. Mapping of Histamine H$_1$ Receptors in the Human Brain Using [$^{11}$C]Pyrilamine and Positron Emission Tomography. J. Neurochem. 1992, 59, 128-136.
Yoon et al. Rapid Screening of Blood-Brain Barrier Penetration of Drugs Using the Immobilized Artificial Membrane Phosphatidylcholine Column Chromatography. J. Biomol. Screen 2006, 11(1), 13-20.
Roberts et al. GABAergic modulation of 5-HT$_7$ receptor-mediated effects on 5-HT efflux in the guinea-pig dorsal raphe nucleus. Neuropharmacology 2004, 46(7), 935-941.
Ohtsuki et al "New Aspects of the Blood-Brain Barrier Transporters; Its Physiological Roles in the Central Nervous System" Biol Pharm Bull 2004 vol. 27(10 pp. 1489-1496.
Pouzet, B. SB-258741: A 5-HT$_7$ Receptor Antagonist of Potential Clinical Interest. CNS Drug Rev. 2002, 8(1), 90-100.
Read et al. Evidence for the involvement of central 5-HT$_7$ receptors in the micturition reflex in anaesthetized female rats. Br. J. Pharmacol. 2003, 140, 53-60.
Read et al. Effects of SB-269970, the 5-HT$_7$ Receptor Antagonist, on Micturition. Presentation Abstract, International Union of Basic & Clinical Pharmacology, XIVth World Congress of Pharmacology, San Francisco, CA, Jul. 2002.
Eglen et al. The 5-HT$_7$ Receptor: Orphan Found. Trends Pharmacol. Sci. 1997, 18, 104-107.
Cheng et al. "Relationship Between the Inhibition Constant (K1) and the Concentration of Inhibitor which Causes 50 Per Cent Inhibition (I50) of an Enzymatic Reaction" Biochem Pharmacol 1973 vol. 22 pp. 3099-3108.
International Search Report for Corresponding International Application No. PCT/US2006/029437 Mailed Jan. 4, 2007, 7 Pgs.
International Search Report for Corresponding International Application No. PCT/US2006/40911 Mailed Sep. 27, 2007, 2 Pgs.
U.S. Appl. No. 60/326,662, Kanamarlapudi et al., Oct. 2, 2001.
U.S. Appl. No. 60/746,497, Deng et al., May 5, 2006.
U.S. Appl. No. 60/806,169, Allison et al., Jun. 29, 2006.
U.S. Appl. No. 60/806,167, Allison et al., Jun. 29, 2006.
U.S. Appl. No. 60/806,165, Keith et al., Jun. 29, 2006.
U.S. Appl. No. 60/938,790, Keith, May 18, 2007.
Appel, M. et al. An analysis of the binding of cocaine analogues to the monamine transporters using tensor decomposition 3-D QSAR. Bioorg. Med. Chem. 2002, 10(5), 1197-1206.
Bard et al. Cloning of a Novel Human Serotonin Receptor (5-HT7) Positively Linked to Adenylate Cyclase. J. Biol. Chem. 1993, 268(31), 23422-23426.
Berge, S.M. et al. Pharmaceutical Salts. J. Pharm. Sci., 1977, 66:1-19.
Bonaventure, P. et al. Radioligand Binding Analysis of Knockout Mice Reveals 5- Hydroxytryptamine, Receptor Distribution and Uncovers 5-Hydroxy-2-(di-Npropylamino)tetralin Interaction with $\alpha_2$ Adrenergic Receptors. Neuroscience 2004, 124, 901-911.
Bonhaus, D.W. et al. Rs-127445: A selective, high affinity, orally bioavailable 5-HT 2B receptor antagonist. Br. J. Pharmacol. 1999, 127(5), 1075-1082.
Bonnet, U. Moclobemide: Evolution, Pharmacokinetic, and Pharmacodynamic Properties. CNS Drug Rev. 2002, 8(3), 283-308.
Bundgaard et al. Design of Prodrugs Ed. H. Bundgaard Elsevier 1985.
Bymaster et al. Fluoxetine, but not other selective serotonin reuptake inhibitors, increases norepinephrine and dopamine extracellular levels in prefrontal cortex. Psychopharmacology (Berlin) 2002, 160(4), 353-361.

Chen et al. P-Glycoprotein Limits the Brain Penetration of Nonsedating but Not Sedating H1-Antagonists. Drug Metab. Dispos. 2003, 31(3), 312-318.
Glennon et al. Higher-End Serotonin Receptors: 5-HT$_5$, 5-HT$_6$, and 5-HT$_7$. J. Med. Chem. 2003, 46(14), 2795-2812.
Greene et al. Protective Groups in Organic Synthesis 1999 3$^{rd}$ Ed. John Wiley & Sons.
Guscott et al. The hypothermic effect of 5-CT in mice is mediated through the 5-HT$_7$, receptor. Neuropharmacology 2003, 44(8), 1031-1037.
Guscott et al. Genetic knockout and pharmacological blockade studies of the 5-HT$_7$ receptor suggest therapeutic potential in depression. Neuropharmacology 2005, 48(4), 492-502.
Hagan et al. Characterization of SB-269970-A, a selective 5-HT7 receptor antagonist. Br. J. Pharmacol. 2000, 13093), 539-548.
Hansen et al. Pharmacological Management of Allergic Rhinitis in the Elderly. Drugs Aging 2005, 2(4), 289-296.
Harsing et al. A 5-HT$_7$ Heteroreceptor-Mediated Inhibition of [$^3$H]Serotonin Release in Raphe Nuclei Slices of the Rat: Evidence for a Serotonergic—Glutamatergic Interaction. Neurochem. Res. 2004, 29(8), 1487-1497.
Hedlund et al. No hypothermic response to serotonin in 5-HT7 receptor knockout mice. Proc. Natl. Acad. Sci. U.S.A. 2003, 100(3), 1375-1380.
Hedlund et al. Functional, molecular and pharmacological advances in 5-HT$_7$ receptor research. Trends Pharmacol. Sci. 2004, 24(9), 481-486.
Hedlund et al. 5-HT$_7$ Receptor Inhibition and Inactivation Induce Antidepressantlike Behavior and Sleep Pattern. Biol. Psychiatry 2005, 58(10), 831-837.
Herrera et al. One-pot synthesis of new heterocycles: 2,4-disubstituted 6,7-dihydro-5H-benzo[6,7]cyclohepta[1,2-d]pyrimidines. Tetrahedron Lett. 2003, 44(10), 2149-2151.
Herrera, A. et al. On the mechanism of reaction between ketones and nitriles. Unexpected results from benzyl nitriles. Tetrahedron 2002, 58(19), 3755-3764.
Herrera, A. et al. 1H and 13C NMR spectral assignments of 2,4-diaryl-substituted cycloalkyl[d]pyrimidines. Magn. Reson. Chem. 2002, 40(4), 293-299.
Herrero et al. "A General and Efficient Pifa Mediated Synthesis of Heterocycle-Fused Quinoline Derivatives" Tetrahedron 2002 vol. 58 pp. 8581-8589.
Hoyer, D. et al. Molecular, pharmacological and functional diversity of 5-Ht receptors. Pharmacol. Biochem. Behay. 2002, 71, 533-554.
Ishiguro et al. Influx and Efflux Transport of H1-Antagonist Epinastine Across the Blood-Brain Barrier. Drug Metab. Dispos. 2004, 32(5), 519-524.
Jerman, J.C. et al. Pharmacological characterisation of human 5-HT2 receptor subtypes. Eur. J. Pharmacol. 2001, 414, 23-30.
Khawam et al. "Side Effects of Antidepressants: An Overview" Cleveland Clinic J. Med 2006 vol. 73(4) pp. 351-361.
Kim et al "Mutation Screening of Human 5-HT28 Receptor Gene in Early-Onset Obsessive-Compulsive Disorder "Molec & Cellular Probes 2000 vol. 14 pp. 4752.
Lafferty et al. The Preparation and Properties of Certain Pyridylpyrimidines and Bidiazines as Potential Chelating Agents for Iron(II). J. Org. Chem. 1967, 32(5), 1591-1596.
Lovenberg et al. A Novel Adenylyl Cyclase-Activating Serotonin Receptor (5-HT$_7$) Implicated in the Regulation of Mammalian Circadian Rhythms. Neuron 1993, 11(3), 449-458.
Marek et al. Synergistic Action of 5-HT$_{2A}$ Antagonists and Selective Serotonin Reuptake Inhibitors in Neuropsychiatric Disorders. Neuropsychopharmacology 2003, 28, 402-412.
Martel et al. Recent advances on the importance of the serotonin transporter Sert in the rat intestine. Pharmacol. Res. 2006, 54, 73-76.
Martinez et al. About the Timing of Wagner-Meerwein and Nametkin Rearrangements, 6,2-Hydride Shift, Proton Elimination and Cation Trapping in 2-Norbornyl Carbocations. Tetrahedron 1998, 54(18), 4607-4614.
May et al. "Evaluation of the Ocular Hypotensive Response of Serotonin 5-HT1A and 5OHT2 Receptor Ligands in Conscious Ocular Hypertensive Cynomolgus Monkeys" J Pharmacol & Experim Therap 2003 vol. 306(1) pp. 301-309.

(56) References Cited

OTHER PUBLICATIONS

McComie et al Protective Groups in Organic Chemistry Ed. J.F.W. McComie Plenum Press 1973.

Mendelson et al "A Review of the Evidence for the Efficacy and Safety of Trazodone in Insomnia" J Clin Psychiatry 2005 vol. 66 pp. 469-476.

Meneses, A. Effects of the 5-$HT_7$ receptor antagonists SB-269970 and DR 4004 in autoshaping Pavlovian/instrumental learning task. Behav. Brain Res. 2004, 155(2), 275-282.

Menza, et al. Modafinil Augmentation of Antidepressant Treatment in Depression. J. Clin. Psychiatry 2000, 61, 378-381.

Murphy et al. Experimental gene interaction studies with SERT mutant mice as models for human polygenic and epistatic traits and disorders. Genes, Brain & Behay. 2003, 2(6), 350-364.

Silvestre et al "Research on adverse drug events. I. Muscarinic M3 receptor binding affinity could predict the risk of antipsychotics to induce type 2 diabetes" Methods Find Exp Clin Pharrnacol 2005 vol. 27(5) pp. 289 -304.

Simons et al. The Pharmacology and Use of H1-Receptor-Antagonist Drugs. N. Engl. J. Med. 1994, 330, 1663-1670.

Spinks et al. Serotonin Reuptake Inhibition: An Update on Current Research Strategies. Curr. Med. Chem. 2002, 9, 799-810.

Stahl et al Essential Psychopharmacology $2^{nd}$. Ed. Cambridge University Press UK 2000.

Stahl et al. Handbook of Pharmaceutical Salts Properties Selections and Use Stahl P.H. Wermuth C.G. Eds Wiley-VCH and VHCA Zurich 2002.

Steru et al. The Automated Tail Suspension Test: A Computerized Device which Differentiates Psychotropic Drugs. Prog. Neuropsychopharmacol. & Biol. Psychiatry 1987, 11(6), 659-671.

Stolle, W.A.W. et al. Intramolecular Diels-Alder reactions of pyrimidines: Synthesis of tricyclic annelated pyridines. Tetrahedron 1989, 45(20), 6511-6518.

Tagawa et al. Neuroimaging of histamine $H_1$ -receptor occupancy in human brain by positron emission tomography (PET): A comparative study of ebastine, a second-generation antihistamine, and (+)-chlorpheniramine, a classical antihistamine. Br. J. Clin. Pharmacol. 2001, 52(5), 501-509.

Tashiro et al. Brain histamine H1 receptor occupancy of orally administered antihistamines measured by positron emission tomography with $^{11}$ C-doxepin in a placebocontrolled crossover study design in healthy subjects: a comparison of olopatadine and ketotifen. Br. J. Clin. Pharmacol. 2006, 61(1), 16-26.

Tashiro et al. Central Effects of Fexofenadine and Cetirizine: Measurement of Psychomotor Performance, Subjective Sleepiness, and Brain Histamine $H_1$ -Receptor Occupancy Using $^{11}$ C-Doxepin Positron Emission Tomography. J. Clin. Pharmacol. 2004, 44(8), 890-900.

Thomas et al. SB-656104-A, a novel selective 5-$HT_7$ receptor antagonist, modulates REM sleep in rats. Br. J. Pharmacol. 2003, 139(4), 705-714.

Thomas et al. [$^3$ H]-Sb-269970 radiolabels 5-HT, receptors in rodent, pig and primate brain tissues. Neuropharmacology 2002, 42(1), 74-81.

Thomas et al. 5-$HT_7$ , Receptors. Curr. Drug Targets CNS Neurol. Disord. 2004, 3(1), 81-90.

To et al. Characterization and distribution of putative 5-$HT_7$ receptors in guinea-pig brain. Br. J. Pharmacol. 1995, 115(1), 107-116.

Tuladhar et al. 5-$HT_7$, receptors mediate the inhibitory effect of 5-HT on peristalsis in the isolated guinea-pig ileum. Br. J. Pharmacol. 2003, 138(7), 1210-1214.

Vanhoenacker et al. 5-$HT_7$, receptors: current knowledge and future prospects. Trends Pharmacol. Sci. 2000, 21, 70-77.

Van Wauwe et al. In Vivo Pharmacology of Astemizole, a New Type of $H_1$-Antihistaminic Compound. Arch. Int. Pharmacodyn. 1981, 251, 39-51.

Varnas et al. Distribution of 5-Ht, receptors in the human brain: a preliminary autoradiographic study using [$^3$H]Sb-269970. Neurosci. Lett. 2004, 367(3), 313-316.

Voitenko, Z.V. et al. Conversions of 2-(2-oxocycloehxylcarbonyl)benzoic acid derivatives to pyrazolo[5,1-a]isoindole and pyrimidine rings. Phosphorus, Sulfur Silicon Relat. Elem. 2005, 180(1), 163-177.

Welch et al. $H_1$ -Antihistamines and the central nervous system. In *Histamine and $H_1$-Antihistamines in Allergic Disease*, $2^{nd}$ ed.; F.E.R. Simons, Ed.; Marcel Dekker, Inc.: New York, 2002; Chapter 11.

Welch et al "H1-Antihistamine and the Central Nervous System" Clin Allergy Immunol 2002 vol. 17 pp. 337-388.

Yanai et al. Histamine $H_1$ receptor occupancy in human brains after single oral doses of histamine $H_1$ antagonists measured by positron emission tomography. Br. J. Pharmacol. 1995, 116, 1649-1655.

Yanai et al. Mapping of Histamine H1 Receptors in the Human Brain Using [$^{11}$ C]Pyrilamine and Positron Emission Tomography. J. Neurochem. 1992, 59, 128-136.

Yoon et al. Rapid Screening of Blood-Brain Barrier Penetration of Drugs Using the Immobilized Artificial Membrane Phosphatidylcholine col. Chromatography. J. Biomol. Screen 2006, 11(1), 13-20.

Kawamura, S. et al. Fused heterocycles, furo[3,2-d]pyrimidines and dihydrocyclopenta[d]pyrimidines, as potential new herbicides. Biosci. Biotechnol. Biochem. 1992, 56(11), 1897-1899.

Keating et al. The effect of a series of organic cations upon the plasmalemmal serotonin transporter, SERT. Life Sci. 2004, 76, 109-119.

Roberts et al. GABAergic modulationof 5-$HT_7$, receptor-mediated effects on 5-HT efflux in the guinea-pig dorsal raphe nucleus. Neuropharmacology 2004, 46(7), 935-941.

Roth, B.L. et al. The Multiplicity of Serotonin Receptors: Uselessly Diverse Molecules or an Embarrassment of Riches? Neuroscientist 2000, 6(4), 252-262.

Sanfilippo et al. Novel tetrahydropyrido[4,3-d]pyrimidines as gastric antilesion agents. Eur. J. Med. Chem. 1992, 27(7), 655-661.

Schotte, A. et al. Risperidone compared with new and reference antipsychotic drugs: in vitro and in vivo receptor binding. Psychopharmacology 1996, 124, 57-73.

Ohtsuki et al " New Aspects of the Blood-Brain Barrier Transporters; Its Physiological Roles in theCentral Nervous System" Biol Pharm Bull 2004 vol. 27(10 pp. 1489-1496.

Olver et al. Third-Generation Antidepressants: Do They Offer Advantages Over the SSRIs? CNS Drugs 2001, 15, 941-954.

Paxinos and Watson the Rat Brain in Stereotaxic Coordinates 1997 Academic Press Index.

Porter, R.H. et al. Functional characterization of agonists at recombinant human 5-HT2A, 5-HT2B and 5-HT2C receptors in Cho-K1 cells. Br. J. Pharmacol. 1999, 128, 13-20.

Poyurovsky et al "Effect of the 5-HT2 Antagonist Mianserin on Cognitive Dysfunction in Chronic Schizophrenia Patients: An Add-On, Double-Blind Placebo-Controlled Study"Euro Neuropsychopharmacol 2003 vol. 13 pp. 123-128.

Pouzet, B. SB-258741: A 5-$HT_7$, Receptor Antagonist of Potential Clinical Interest. CNS Drug Rev. 2002, 8(1), 90-100.

Read et al. Evidence for the involvement of central 5-$HT_7$, receptors in the micturition reflex in anaesthetized female rats. Br. J. Pharmacol. 2003, 140, 53-60.

Read et al. Effects of SB-269970, the 5-$HT_7$, Receptor Antagonist, on Micturition. Presentation Abstract, International Union of Basic & Clinical Pharmacology, XIVth World Congress of Pharmacology, San Francisco, CA, Jul. 2002.

Eglen et al. The 5-$HT_7$, Receptor: Orphan Found. Trends Pharmacol. Sci. 1997, 18, 104-107.

Frazer, A. Serotonergic and Noradrenergic Reuptake Inhibitors: Prediction of Clinical Effects from In Vitro Potencies. J. Clin. Psychiatry 2001, 62 Suppl. 12, 16-23.

Glass et al. Midbrain Raphe Modulation of Nonphotic Circadian Clock Resetting and 5-HT Release in the Mammalian Suprachiasmatic Nucleus. J. Neurosci. 2003, 23(20), 7451-7460.

DeRuiter, J. et al. Investigation of the Synthesis and Analgesic Activity of 1-Substituted 4-(Propananilido)perhydroazepines. J. Het. Chem. 1992, 29(4), 779-786.

Dube, H. et al. Synthesis of chiral alpha-aminoalkylpyrimidines using an enantioselective three-component reaction. Synthesis 2004, 12, 2015-2025.

(56) References Cited

OTHER PUBLICATIONS

Collier et al. Applications of Nitriles as Reagents for Organic Synthesis with the Loss of the Nitrile Functionality (including Cycloaddition Reactions). Science of Synthesis 2004, 19, 403-425.

Cheng et al. "Relationship Between the Inhibition Constant (K1) and the Concentration of Inhibitor which Causes 50 Per Cent Inhibition (I50) of an Enzymatic Reaction" Biochem Pharmacol 1973 vol. 22 pp. 3099-3108.

Kast et al "Mirtazapine May Be Useful in Treating Nausea and Insomnia of Cancer Therapy" Support Care Center 2001 vol. 9 pp. 469-470.

Ni et al. 5-Hydroxytryptamine in the Cardiovascular System: Focus on the Serotonin Transporter (SERT). Clin. Exp. Pharmacol. Physiol. 2006, 33(7), 575-583.

Narajo et al. "Ritanserin a Central 5-HT2 Antagonist, in Heavy Social Drinkers: Desire to Drink, Alcohol Intake and Related Effects" Addiction 1985 vol. 90(7) pp. 893-905.

* P<0.05 v. Vehicle+Vehicle
** P<0.01 v. Vehicle+Vehicle
***P<0.001 v. Vehicle+Vehicle
# P<0.05 v. JNJ-18038683+Vehicle

** P<0.01 v. Vehicle+Vehicle, JNJ18038683+Vehicle, and Vehicle+Citalopram

* P<0.05 v. Vehicle+Vehicle
** P<0.01 v. Vehicle+Vehicle
***P<0.001 v. Vehicle+Vehicle
# P<0.05 v. SB-269970+Vehicle and Vehicle+Citalopram

* P<0.05 v. Vehicle+Vehicle
** P<0.01 v. Vehicle+Citalopram
***P<0.001 v. Vehicle+Vehicle
# P<0.05 v. SB-269970+Vehicle

** P<0.01 v. Vehicle+Vehicle
*** P<0.001 v. Vehicle+Citalopram

* P<0.05 v. Vehicle+Vehicle

COMBINATION OF 5-HT7 RECEPTOR ANTAGONIST AND SEROTONIN REUPTAKE INHIBITOR THERAPY

CROSS-REFERENCE TO RELATED APPLICATIONS

This application is a continuation-in-part of U.S. patent application Ser. No. 11/460,294, filed Jul. 27, 2006, now U.S. Pat. No. 7,598,255 the disclosure of which is incorporated by reference herein, which application claims priority to U.S. Provisional Application No. 60/705,719, filed Aug. 4, 2005.

FIELD OF THE INVENTION

The present invention relates to methods and pharmaceutical compositions for treating serotonin-mediated diseases and conditions by administering an effective combined amount of a 5-hydroxytryptamine receptor 7 (5-HT7 receptor) antagonist and a serotonin reuptake inhibitor (SRI).

BACKGROUND OF THE INVENTION

The following background discussion is provided to facilitate a better appreciation of the technology relating to the invention. As statements in this discussion may reflect viewpoints of an inventor, they should not be misconstrued as necessarily corresponding to knowledge in the prior art.

Serotonin (5-hydroxytryptamine, 5-HT) is a major neurotransmitter eliciting effects via a multiplicity of receptors. To date, at least fifteen different 5-HT receptors have been identified (Marek et al., *Neuropsychopharmacology* (2003), 28:402-412), largely as the result of cloning cDNAs, and these receptors have been grouped into seven families (5-HT1 through 5-HT7) (Hoyer et al., *Pharmacol. Biochem. Behav.* (2002), 71:533-554). Fourteen of the fifteen cloned 5-HT receptors are expressed in the brain. Aberrant 5-HT availability or activity is implicated in various disease states, including: certain disorders of the central nervous system (CNS), such as depression, anxiety, schizophrenia, mood disorders, drug and alcohol dependence and addiction disorders; sleep disorders, jet lag, and sleep/wake disturbances; eating disorders; mood disorders; obsessive compulsive disorder; learning and memory dysfunction; migraine; chronic pain; temperature dysregulation; nociception; neurogenic inflammation; sexual dysfunction; cardiovascular disorders; vascular and hypertensive disorders; gastric disorders; irritable bowel disorders, urinary incontinence, hormone secretion, and cognition; and metabolic disorders. The identification of multiple 5-HT receptors has provided an opportunity to characterize existing therapeutic agents thought to act via the serotonergic system.

The 5-HT7 receptor is the most recently described member of the large family of serotonin receptors (see, e.g., Bard et al., *J. Biol. Chem.* (1993), 268(31):23422-23426; Hedlund et al., *Trends in Pharmacol. Sci.* (2004), 25(9):481-486; and Lovenberg et al., *Neuron* (1993), 11(3): 449-458). In the rodent and human brain, the highest receptor densities were found in the thalamus, hypothalamus (including the suprachiasmatic nucleus), amygdala, hippocampus, cortex and dorsal raphe (Bonaventure et al., *Neuroscience* (2004), 124(4):901-911; Thomas et al., *Neuropharmacology* (2002), 42(1):74-81; To et al., *Br. J. Pharmacol.* (1995), 115(1):107-116; and Varnas et al., *Neurosci. Lett.* (2004), 367(3):313-316). The 5-HT7 receptor has also been detected in the periphery, where it is found primarily in smooth muscle cells of blood vessels (Bard et al., *J. Biol. Chem.* (1993), 268(31):23422-23426), and in the gastrointestinal tract, where it is involved in peristalsis (Tuladhar et al., *Br. J. Pharmacol.* (2003), 138(7):1210-1214).

Recently discovered antagonists for the 5-HT7 receptor and knockout mice have been helpful for elucidating the receptor's role in several physiological and pathophysiological phenomena (see, e.g., Hedlund et al., *Trends in Pharmacol. Sci.* (2004), 25(9):481-486 and US Patent Application Publication No. 2005/0119295). Important functional roles for the 5-HT7 receptor have been established in thermoregulation, circadian rhythm, learning and memory, hippocampal signaling, sleep, and micturition (Glass et al., *J. Neurosci.* (2003), 23(20):7451-7460; Guscott et al., *Neuropharmacology* (2003), 44 (8):1031-1037; Hagan et al., *Br. J. Pharmacol.* (2000), 130(3):539-548; Hedlund et al., *Proc. Natl. Acad. Sci. USA* (2003), 100(3):1375-1380; Meneses, A., *Behav. Brain Res.* (2004), 155(2):275-282; and Read et al. *IUPHAR* Meeting (2002), San Francisco, Calif., USA).

The 5-HT7 receptor is implicated in circadian rhythm phase resetting, and two selective 5-HT7 receptor-selective antagonists (SB269970 and SB656104) have been shown to induce change in sleep parameters in a pattern opposite from those in patients with clinical depression. In wild type mice, SB269970 decreased immobility in both tail suspension and forced swim test, two tests used as predictor of antidepressant activity (Guscott et al. (2005), *Neuropharmacology*, 48(4): 492-502; and Hedlund et al. (2005), *Biol. Psychiatry*, 58(10): 831-837). When administered at the beginning of the sleep phase, both SB269970 and SB656104 increased the latency to rapid eye movement (REM) sleep and decreased the amount of time spent in REM sleep (Hagan et al., *Br. J. Pharmacol.* (2000), 130(3):539-548 and Thomas et al., *Br. J. Pharmacol.* (2003), 139(4):705-714). In addition, 5-HT7 knockout mice showed reduced immobility in both the forced swim and the tail suspension tests and spent less time in and had less frequent episodes of REM sleep, also consistent with an antidepressant like state (Hedlund et al., *Biol. Psychiatry* (2005), 58(10):831-837).

Some current treatments for depression exhibit considerable delay between start of treatment and subjective improvement. Many drugs do not cause an improvement in the Hamilton Rating Scale for Depression until after several weeks of treatment. Various drugs that are now available have a limited response rate and in some clinical trials only about 30% of patients show clinical improvement (Menza et al., *J. Clin. Psych.* (2000), 61:378-381). Psychiatrists frequently have to evaluate several drugs for individual patients before a satisfactory therapeutic response is observed.

Current clinical treatment of depression typically involves a drug selected from one of four types of drugs: 1) monoamine oxidase (MAO) inhibitors; 2) tricyclic antidepressants (TCA); 3) selective serotonin reuptake inhibitors (SSRIs); and 4) other drugs such as reboxetine and venlafaxine. MAOs have long been used as second-line drugs because of their potentially dangerous side effects; but more recently, reversible MAO-A selective inhibitors with improved profiles have been described (Bonnet, *CNS Drug Reviews* (2002), 8:283-308). TCAs such as amitryptiline display complex pharmacological activities. They inhibit reuptake of noradrenaline and serotonin via their respective transporters, but also have affinity at muscarinic and histamine $H_1$ receptors. Thus, their efficacy in treating depression is counterbalanced by numerous unwanted side effects. The SSRIs, which represent a large and successful class of antidepressants (see, e.g., Spinks, *Current Med. Chem.* (2002), 9:799-810), show a higher selectivity for the serotonin transporter (SERT) than for the norepinephrine transporter (NET), although the exact affinity ratio varies from drug to drug. This class of drugs is typically characterized by a milder side-effect profile than the MAO-inhibitors or the TCAs. Other drugs have been described, such as reboxetine, which preferentially targets the NET, and venlafaxine, which has dual activity at the SERT and NET (Olver et al., *CNS Drugs* (2001), 15: 941-954).

Although progress has been made in the treatment of various diseases and disorders associated with aberrant 5-HT function, there remains a desire for improved therapies.

SUMMARY OF THE INVENTION

Recent data suggest that there is a complex interaction between 5-HT7 receptors and glutamatergic neurons in the raphe nuclei that influences the activity of the 5-HT neurons (see, e.g., Harsing et al., *Neurochem. Res.* (2004), 29(8): 1487-1497 and Roberts et al., *Neuropharmacology* (2004), 46(7), 935-941). The axon terminals of the glutamatergic corticoraphe neurons may possess 5-HT7 receptors. Activation of these 5-HT7 receptors inhibits glutamate release, which consequently leads to decreased activity of serotonergic neurons. Blockade of 5-HT7 receptors may lead to an increased activity of serotonergic neurons.

The administration of a 5-HT7 receptor antagonist may therefore augment effects achieved with administration of another serotonergic agent, such as a selective SRI (SSRI). Indeed, experiments described herein reflect that administration of both a 5-HT7 receptor antagonist and an SRI can yield an advantageous complementary effect useful in and in treating serotonin-mediated diseases and conditions. Thus, the invention is directed to general and preferred embodiments of methods and pharmaceutical compositions for treating or preventing serotonin-mediated diseases or conditions as defined herein. Additional preferred embodiments, features, and advantages of the invention will be apparent from the following detailed description taken in conjunction with the drawing figures.

BRIEF DESCRIPTION OF THE DRAWINGS

In FIG. 1A, *=p<0.05 vs. vehicle group, =p<0.01 vs. vehicle group, *=p<0.001 vs. vehicle group, ^=p<0.05 vs. 1 mg/kg SB269970 group, and #=p<0.001 vs. 1 mg/kg SB269970 group. In FIG. 1B, *p<0.05 vs. vehicle group, **=p<0.01 vs. vehicle group, and ^=p<0.01 vs. 0.1 mg/kg Compound A group.

In FIGS. 5A and 5C, data bars represent the mean±SEM; n=3-4. In FIGS. 5B and 5D, area under the curve (AUC) values of data in FIGS. 5A and 5B, respectively, are presented. ***=p<0.001 vs. vehicle; #=p<0.01 vs. citalopram alone.

In FIGS. 6A and 6C, data bars represent the mean±SEM; n=3-4. In FIGS. 6B and 6D, area under the curve (AUC) values of data in FIGS. 6A and 6B, respectively, are presented. ***=p<0.01 vs. vehicle.

DETAILED DESCRIPTION OF INVENTION AND ITS PREFERRED EMBODIMENTS

Figure 1A:
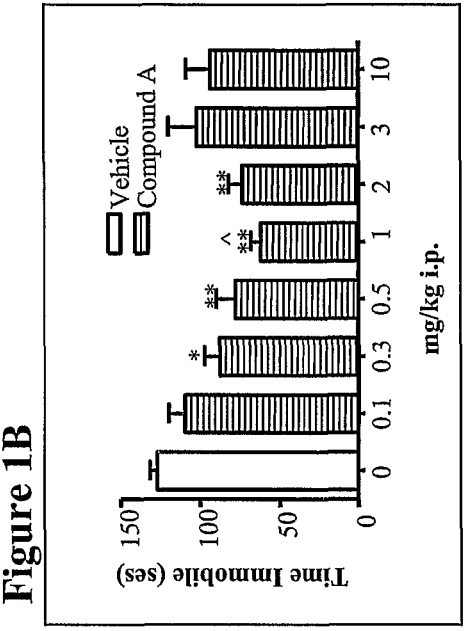
FIGS. 1A and 1B depict effects of administration of the indicated doses of each of the 5-HT7 receptor antagonists, (R)-3-[2-[2-(4-methylpiperidin-1-yl)ethyl]pyrrolidine-1-sulfonyl]phenol hydrochloride (SB269970) and 1-benzyl-3-(4-chloro-phenyl)-1,4,5,6,7,8-hexahydro-1,2,6-triaza-azulene (Compound A), independently on mice in the setting of the tail suspension test (FIGS. 1A and 1B, respectively). Data bars represent the mean±standard error of the mean (SEM) and n=8.

For the sake of brevity, the disclosures of all patents and other publications cited in this specification are incorporated by reference herein.

In one embodiment, the invention relates to a method of treating a subject suffering from or diagnosed with a serotonin-mediated disease or condition, comprising administering to a subject in need of such treatment: an amount of a 5-HT7 receptor antagonist and an amount of an SRI and a 5-HT7 receptor antagonist, the amounts together providing an effective combined amount. In another embodiment, the invention relates to a pharmaceutical composition for treating a serotonin-mediated disease or condition, comprising: (a) (i) an amount of a 5-HT7 receptor antagonist, and (ii) an amount of a selective serotonin reuptake inhibitor, such amounts together providing an effective combined amount; and (b) a pharmaceutically acceptable excipient.

The terms "including", "containing", and "comprising" are used herein in their open, non-limiting sense.

The term "subject" refers to a mammalian patient in need of therapeutic or prophylactic treatment. Preferably, subjects treated in accordance with the invention are human.

The term "treat" or "treating" is intended to refer to administration of a composition to a subject for the therapeutic or prophylactic benefit of reversing, ameliorating, alleviating, inhibiting the progress of, lessening the severity of, or preventing a disease, medical condition, or disorder. Symptoms and disease states are intended to be included within the scope of diseases, conditions, and disorders.

In accordance with the invention, effective amounts of an SRI and a 5-HT7 receptor antagonist are administered to a subject to treat serotonin-mediated diseases and conditions (or their associated symptoms) that are mediated through increasing the release of serotonin, inhibiting its reuptake, or both, or by increasing activity of serotonergic neurons, such as those associated with aberrant 5-HT7 receptor levels or serotonin reuptake activity or function. Exemplary medical conditions, diseases, and disorders include cognitive and psychiatric disorders, sleep disorders, vascular disorders, gastrointestinal disorders, urinary incontinence, aberrant hormone secretion, metabolic disorders, septic shock, renal disorders, inflammation and inflammatory disorders (see, e.g., Hedlund et al., *Trends Pharmacol. Sci.* (2004), 25(9): 481-486; Thomas et al., *Curr. Drug Targets CNS Neurol. Disord.*, (2004), 3(1):81-90; Pouzaet B, *CNS Drug Rev.*, (2002), 8(1):90-100; Eglen et al., *TiPS* (1997), 18:104-107; Vanhoenacker et al., *TiPS* (2000), 21:70-77; Glennon R A, *J. Med. Chem.* (2003), 46(14):2795-2812; Ni et al., *Clin. Exp. Pharmacol. Physiol* (2006), 33(7):575-583; Martel F, *Pharmacol. Res.* (2006), 54:73-76; and Murphy et al., *Genes, Brain & Behav.* (2003), 2(6):350-364.

Cognitive and psychiatric disorders include depression/anxiety, generalized anxiety disorder, schizophrenia, bipolar disorders, psychotic disorders, obsessive-compulsive disorder, mood disorders, post-traumatic stress and other stress-related disorders, learning and memory dysfunction, migraine, disorders associated with nociception and pain, arousal and vigilance disorders, disorders associated with aberrant sensory perception, disorders associated with aberrant motor activity, disorders associated aberrant thermoregulation, sexual dysfunction, centrally mediated hypotension, alcohol abuse, drug abuse, and other addictive disorders, metabolic disorders, hormonal imbalances, eating disorders, and obesity.

Sleep disorders include insomnia, disturbed sleep, narcolepsy (with or without associated cataplexy), cataplexy, sleep/wake disturbances, idiopathic somnolence, excessive daytime sleepiness (EDS), circadian rhythm disorders, fatigue, lethargy, and jet lag. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

Vascular disorders include cardiovascular disorders, cardiovascular shock and arrhythmias, hypotension, ischemias, and stroke.

Gastrointestinal disorders include gastric motility disorders, diarrhea, spastic colon and irritable bowel disorders.

In addition, combination therapies of the present invention may be used in the treatment or prevention of various ocular disorders including glaucoma, optic neuritis, diabetic retinopathy, retinal edema, and age-related macular degeneration.

In certain preferred embodiments, the serotonin-mediated disease or disorder is selected from depression, anxiety, sleep or wake disturbances, jet-lag, migraine, urinary incontinence, gastric motility, and irritable bowel disorders.

The term "effective combined amount" means an effective or complementary amount or dose of a 5-HT7 receptor antagonist and an effective or complementary amount of an SRI that together are sufficient to generally bring about or effect a desired therapeutic or prophylactic benefit to patients in need of treatment of a serotonin-mediated disease or condition. The benefit of the effective combined amount of the two agents may be advantageously supra-additive or synergistic, relative to the benefit that would be achieved by administration of the same total amount (i.e., the numerical amount equivalent to the combined effective amount) of one of the agents administered alone, or it may be ameliorative (i.e., the amount of one agent may lessen or reverse an undesirable effect typically induced by administration of the other agent alone).

The term "effective amount" means an amount or dose of a 5-HT7 receptor antagonist agent or an SRI agent (as the case may be) that is sufficient to generally bring about or effect a therapeutic or prophylactic benefit when administered alone to patients in need of treatment of a serotonin-mediated disease or condition.

The term "complementary amount" means an amount or dose of a 5-HT7 receptor antagonist agent or an SRI agent (as the case may be) that is: (i) a potentiating amount, which is a dose insufficient to generally bring about or effect the therapeutic or prophylactic benefit when administered alone to patients in need of treatment of a serotonin-mediated disease or condition (i.e., it is sub-efficacious) but which potentiates or augments the effect of the other 5-HT-mediating agent (the SRI or 5-HT7 receptor antagonist, as the case may be) with which it is administered; and/or (ii) an ameliorative amount, which is a dose of one agent that is sufficient to reverse or lessen the severity of an undesirable side effect generally caused by administration of the other agent alone.

In certain embodiments, an effective amount of a 5-HT7 receptor antagonist may be combined with an effective amount of an SRI to provide a therapeutic composition comprising an effective combined amount of the two agents. In preferred embodiments, an effective amount of a 5-HT7 receptor antagonist agent is combined with a complementary amount of an SRI agent to provide a therapeutic composition comprising an effective combined amount of the two agents. In other preferred embodiments, an effective amount of an SRI is combined with a complementary amount of a 5-HT7 receptor antagonist to provide a therapeutic composition comprising an effective combined amount of the two agents. In an especially preferred embodiment, an effective amount of an SSRI such as citalopram is combined with a complementary amount of a 5-HT7 receptor antagonist sufficient to ameliorate an increase in sleep fragmentation induced by the SSRI, more preferably, to also potentiate the effect of the SSRI.

Suitable amounts of the 5-HT7 receptor antagonists and SRIs, individually and together, may be ascertained by routine methods, such as modeling, dose escalation studies, or other clinical trials, and by taking into consideration routine factors, e.g., the mode or route of administration or drug delivery, the pharmacokinetics of the agent, the severity and course of the disease, disorder, or condition, the subject's previous or ongoing therapy, the subjects weight, health status, and response to drugs, and the judgment of the treating physician. An exemplary oral dose is in the range of from about 0.001 to about 200 mg of each 5-HT7 receptor antagonist agent and SRI per kg of subject's body weight per 24 hours, or preferably about 0.05 to 100 mg/kg/day, or about 1 to 50 mg/kg/day, in single or divided dosage units (e.g., BID, TID, QID). For a 70-kg human, an illustrative range for a dosage amount is from about 0.05 to about 7 g/day, or about 0.2 to about 2.5 g/day, or about 0.01 to about 1 g/day, or about 0.001 to about 0.5 g/day, of each active agent, either in separate dosage forms or in a combined dosage form. Infusion doses can range from about 1 to 1000 μg/kg/min of each agent, admixed with a pharmaceutical carrier over a period ranging from several minutes to several days. For an exemplary topical administration, the active agents may be admixed with a pharmaceutical carrier at a concentration of about 0.1% to about 10% of drug to vehicle. Other suitable dosages for the active ingredients or agents may be routinely determined, e.g., in light of the dosages for 5-HT7 receptor antagonists and SRIs exemplified in the art and in investigative and commercial products. For additional guidance, see, e.g., Simons et al., *New England J Medicine* (1994), 330: 1663-1670.

Once improvement of the disease or condition has occurred, the dose may be adjusted for preventative or maintenance treatment, if indicated. For example, the dosage or the frequency of administration, or both, may be reduced as a function of the reduction of intensity or frequency of symptoms, to a level at which the desired therapeutic or prophylactic effect is maintained. Of course, if the medical condition has been alleviated to an appropriate level, treatment may cease. Patients may, however, be intermittently treated on a long-term basis with the combination therapy of the invention upon any recurrence of the medical condition or symptoms thereof.

The combination therapies of the present invention may be used to treat various serotonin-mediated diseases and conditions, such as those associated with 5-HT activity in either peripheral systems or central nervous systems. For diseases and conditions in which the CNS is involved, the selected 5-HT7 receptor antagonist and/or SRI preferably possess centrally acting characteristics. Centrally acting 5-HT7 receptor antagonists and SRIs are those that readily enter the central nervous system (CNS) across the blood-brain barrier (BBB) or have high BBB permeability. See, e.g., Frazer A, *J. Clin. Psychiatry* (2001), 62 Suppl. 12:16-23, Ohtsuki S, *Biol. Pharm. Bull.* (2004), 27(10): 1489-1496; Ishiguro et al., *Drug Metabolism & Disposition* (2004), 32(5): 519-524; Hansen et al., *Drugs Aging* (2005), 22(4): 289-96; Welch et al., *Clin. Allergy Immunol.* (2002), 17: 337-88.

Compounds having 5-HT7 receptor antagonizing activity or SRI activity that are known or that become available may be tested for central activity (i.e., to determine if they are centrally acting) by measuring their ability to cause, for example, anti-depressive effects in humans. A 5-HT7 receptor antagonist or SRI that is positive in such a screen, i.e., that causes significant anti-depressive effects in humans, is one that may be selected for use in the invention. Alternatively, to screen compounds for 5-HT7 receptor antagonizing activity or SRI activity useful in the invention artisans may directly measure the binding of such compounds to human brain 5-HT7 receptors or SERT in vivo using positron emission tomography (PET) (see, e.g., Yanai et al., *Br. J. Pharmacol.* (1995), 116:1649-1655; Yania et al., *J. Neurochem.* (1992), 59:128-136; Tagawa et al., *Br. J. Clin. Pharmacol.* (2001), 52(5): 501; and Tashiro et al., *British J. Clin. Pharmacology* (2005), 61(1): 16-26). In another technique, this property may be measured in animals, e.g., by quantitating the amount of the candidate 5-HT7 receptor antagonist or SRI compound in the brain by LC/MS after oral dosing (Chen et al., *Drug Metabolism and Disposition* (2003), 31:312-318). In another assay employing animals, the ratio of therapeutic dose to lethal dose in guinea pigs may be used as a measure of central activity, where brain penetration decreases as ratios increase (Van Wauwe et al., *Arch. Int. Pharmacodyn. Ther.* (1982), 251:39-51). Alternatively, 5-HT7 receptor antagonist and SRI candidate compounds may be assayed for activity by testing their ability to inhibit the in vitro binding of known high affinity 5-HT7 receptor-binding or SERT-binding compounds, respectively.

Another in vitro method for screening for centrally acting compounds is the immobilized artificial membrane phosphatidylcholine column chromatography test described by Yoon et al., *J. Biomolecular Screening* (2006), 11(1):13-20. Alternatively, a battery of tests may be employed, such as the subjective sleepiness test (evaluated by Stanford Sleepiness Scale), objective psychomotor test, and measurement of histamine $H_1$-receptor occupancy in the brain as described by Tashiro et al., *J. Clinical Pharmacology* (2004), 44:890-900.

Suitable 5-HT7 receptor antagonists may also be selected from the various compounds known in the art having 5-HT7 receptor antagonistic activity. Exemplary 5-HT7 receptor-binding compounds include 5-HT, carboxamidotryptamine (5-CT), metergoline, methiothepin, methysergide, 2-Br lysergic acid diethylamide (2-Br LSD), 1-naphthylpiperazine, and clozapine (see, e.g., Glennon et al., *J. Med. Chem.* (2003), 46(14):2795-2812) and radiolabeled forms of these compounds. Exemplary SRIs include SERT-binding compounds or SSRIs such as fluoxetine, citalopram, fluvoxamine, paroxetine and sertraline, quinidine, verapamil, propranolol, amiloride, nicotine, clonidine, cocaine, amphetamine, and (+)-3,4-methylene-dioxymethamphetamine (MDMA) (see, e.g., Martel, *Pharmacol. Research* (2006), 54:73-76; and Keating et al., *Life Sci* (2004), 76:109-119).

In preferred embodiments, the 5-HT7 receptor antagonist of the combination therapy of the invention is selected from the 5-HT7 antagonist compounds specifically described or from the species covered by the general structural formulae in: U.S. Pat. No. 6,025,367; US Patent Application Publication No. 2005/0119295; U.S. patent application Ser. No. 11/460,294, filed Jul. 27, 2006 ; International Publication Nos. WO 2005/040169, WO 2005/005387, WO 2002/062788, WO 2001/57039, WO 2001/029029, WO 2000/73299, WO 2000/056712, WO 2000/037082, WO 99/54303, WO 99/24022, WO 99/22804, WO 98/00400, WO 98/31354, WO 97/49695, WO 97/48681, WO 97/29097, and WO 96/32944; and EP 937715; the disclosures of which are incorporated by reference herein.

Additionally, preferred 5-HT7 receptor antagonists are those described in US Patent Application Publication No. 2005/0119295 and U.S. Provisional Patent Application No. 60/746,497, filed May 5, 2006 possessing activity ($K_i$) against the 5-HT7 receptor≤1000 nM. Particularly preferred 5-HT7 receptor antagonists are selected from the compounds listed below and their pharmaceutically acceptable salts (where a free acid or base is listed) or free acid/base form (where a salt is listed):

1-Benzyl-3-(4-nitro-phenyl)-4,5,6,7-tetrahydro-1H-pyrrolo [3,2-c]pyridine;
1-Benzyl-3-(5-chloro-thiophen-2-yl)-4,5,6,7-tetrahydro-1H-pyrrolo[3,2-c]pyridine;

1-Benzyl-3-thiophen-2-yl-4,5,6,7-tetrahydro-1H-pyrrolo[3,2-c]pyridine;
1-(3-Chloro-benzyl)-3-phenyl-4,5,6,7-tetrahydro-1H-pyrrolo[3,2-c]pyridine;
1-Benzyl-3-(3-fluoro-phenyl)-4,5,6,7-tetrahydro-1H-pyrrolo[3,2-c]pyridine;
3-(4-Chloro-phenyl)-1-(2-fluoro-benzyl)-4,5,6,7-tetrahydro-1H-pyrrolo[3,2-c]pyridine;
1-(3-Chloro-benzyl)-3-(4-chloro-phenyl)-4,5,6,7-tetrahydro-1H-pyrrolo[3,2-c]pyridine;
1-(2-Chloro-benzyl)-3-phenyl-4,5,6,7-tetrahydro-1H-pyrrolo[3,2-c]pyridine;
1-(4-Chloro-benzyl)-3-(4-chloro-phenyl)-4,5,6,7-tetrahydro-1H-pyrrolo[3,2-c]pyridine;
1-Benzyl-3-(2,4-dichloro-phenyl)-4,5,6,7-tetrahydro-1H-pyrrolo[3,2-c]pyridine;
1-(4-Methoxy-benzyl)-3-phenyl-4,5,6,7-tetrahydro-1H-pyrrolo[3,2-c]pyridine;
1-Benzyl-2-methyl-3-phenyl-4,5,6,7-tetrahydro-1H-pyrrolo[3,2-c]pyridine;
1-Benzyl-3-p-tolyl-4,5,6,7-tetrahydro-1H-pyrrolo[3,2-c]pyridine;
3-Benzo[1,3]dioxol-5-yl-1-benzyl-4,5,6,7-tetrahydro-1H-pyrrolo[3,2-c]pyridine;
1-Benzyl-3-(4-fluoro-phenyl)-4,5,6,7-tetrahydro-1H-pyrrolo[3,2-c]pyridine;
1-Butyl-3-p-tolyl-4,5,6,7-tetrahydro-1H-pyrrolo[3,2-c]pyridine;
1-Benzyl-3-(4-bromo-phenyl)-4,5,6,7-tetrahydro-1H-pyrrolo[3,2-c]pyridine;
1-Benzyl-3-(4-trifluoromethyl-phenyl)-4,5,6,7-tetrahydro-1H-pyrrolo[3,2-c]pyridine;
1-Benzyl-3-(4-chloro-phenyl)-4,5,6,7-tetrahydro-1H-pyrrolo[3,2-c]pyridine;
1-Benzyl-3-phenyl-1,4,5,6,7,8-hexahydro-pyrrolo[2,3-d]azepine;
1-Benzyl-3-(5-methyl-thiophen-2-yl)-4,5,6,7-tetrahydro-1H-pyrrolo[3,2-c]pyridine;
1-Benzyl-3-(4-chloro-phenyl)-1,4,5,6,7,8-hexahydro-pyrrolo[2,3-d]azepine;
1-Benzyl-3-(5-chloro-thiophen-2-yl)-1,4,5,6,7,8-hexahydro-pyrrolo[2,3-d]azepine;
1-(4-Chloro-benzyl)-3-phenyl-4,5,6,7-tetrahydro-1H-pyrrolo[3,2-c]pyridine;
1-Benzyl-3-phenyl-4,5,6,7-tetrahydro-1H-pyrrolo[3,2-c]pyridine;
1-Benzyl-3-(3-chloro-phenyl)-1,4,5,6,7,8-hexahydro-pyrrolo[2,3-d]azepine;
1-Benzyl-3-(4-methoxy-phenyl)-4,5,6,7-tetrahydro-1H-pyrrolo[3,2-c]pyridine;
1-Benzyl-3-(4-chloro-phenyl)-5-ethyl-4,5,6,7-tetrahydro-1H-pyrrolo[3,2-c]pyridine;
1-Benzyl-3-(4-chloro-phenyl)-5-isopropyl-4,5,6,7-tetrahydro-1H-pyrrolo[3,2-c]pyridine;
1-Benzyl-3-(4-chloro-phenyl)-5-methyl-4,5,6,7-tetrahydro-1H-pyrrolo[3,2-c]pyridine;
1-Benzyl-3-(3-chloro-4-fluoro-phenyl)-5-methyl-4,5,6,7-tetrahydro-1H-pyrrolo[3,2-c]pyridine;
1-Benzyl-5-isopropyl-3-phenyl-4,5,6,7-tetrahydro-1H-pyrrolo[3,2-c]pyridine;
1-Benzyl-3-(4-trifluoromethyl-phenyl)-1,4,5,6,7,8-hexahydro-1,2,6-triaza-azulene;
1-Benzyl-3-phenyl-1,4,5,6,7,8-hexahydro-1,2,6-triaza-azulene;
1-Benzyl-3-(2-fluoro-phenyl)-1,4,5,6,7,8-hexahydro-1,2,6-triaza-azulene;
1-Benzyl-3-(3-fluoro-phenyl)-1,4,5,6,7,8-hexahydro-1,2,6-triaza-azulene;
1-Benzyl-3-(4-fluoro-phenyl)-1,4,5,6,7,8-hexahydro-1,2,6-triaza-azulene;
1-Benzyl-3-(3,4-dichloro-phenyl)-1,4,5,6,7,8-hexahydro-1,2,6-triaza-azulene;
1-[4-(1-Benzyl-1,4,5,6,7,8-hexahydro-1,2,6-triaza-azulen-3-yl)-phenyl]-ethanone;
1-Benzyl-3-(4-trifluoromethoxy-phenyl)-1,4,5,6,7,8-hexahydro-1,2,6-triaza-azulene;
1-Benzyl-3-(3-chloro-phenyl)-1,4,5,6,7,8-hexahydro-1,2,6-triaza-azulene;
4-(1-Benzyl-1,4,5,6,7,8-hexahydro-1,2,6-triaza-azulen-3-yl)-benzonitrile;
1-(4-Chloro-benzyl)-3-phenyl-1,4,5,6,7,8-hexahydro-1,2,6-triaza-azulene;
1-(4-Chloro-benzyl)-3-(4-chloro-phenyl)-1,4,5,6,7,8-hexahydro-1,2,6-triaza-azulene;
1-Benzyl-3-phenyl-6-propyl-1,4,5,6,7,8-hexahydro-1,2,6-triaza-azulene;
1-Benzyl-6-isopropyl-3-phenyl-1,4,5,6,7,8-hexahydro-1,2,6-triaza-azulene;
1-Benzyl-3-(4-chloro-phenyl)-1,4,5,6,7,8-hexahydro-1,2,6-triaza-azulene;
1-Benzyl-3-(4-chloro-phenyl)-1,4,5,6,7,8-hexahydro-1,2,5-triaza-azulene;
3-(4-Chloro-phenyl)-1-methyl-1,4,5,6,7,8-hexahydro-1,2,6-triaza-azulene;
3-(4-Chloro-phenyl)-2-methyl-2,4,5,6,7,8-hexahydro-1,2,6-triaza-azulene;
3-(4-Chloro-phenyl)-1-ethyl-1,4,5,6,7,8-hexahydro-1,2,6-triaza-azulene;
3-(4-Chloro-phenyl)-2-ethyl-2,4,5,6,7,8-hexahydro-1,2,6-triaza-azulene;
3-(4-Chloro-phenyl)-1-propyl-1,4,5,6,7,8-hexahydro-1,2,6-triaza-azulene;
3-(4-Chloro-phenyl)-2-propyl-2,4,5,6,7,8-hexahydro-1,2,6-triaza-azulene;
1-Butyl-3-(4-chloro-phenyl)-1,4,5,6,7,8-hexahydro-1,2,6-triaza-azulene;
2-Butyl-3-(4-chloro-phenyl)-2,4,5,6,7,8-hexahydro-1,2,6-triaza-azulene;
3-(4-Chloro-phenyl)-1-(2-cyclohexyl-ethyl)-1,4,5,6,7,8-hexahydro-1,2,6-triaza-azulene;
3-(4-Chloro-phenyl)-2-(2-cyclohexyl-ethyl)-2,4,5,6,7,8-hexahydro-1,2,6-triaza-azulene;
3-(4-Chloro-phenyl)-1-phenethyl-1,4,5,6,7,8-hexahydro-1,2,6-triaza-azulene;
3-(4-Chloro-phenyl)-2-phenethyl-2,4,5,6,7,8-hexahydro-1,2,6-triaza-azulene;
3-(4-Chloro-phenyl)-1-(4-fluoro-3-methyl-benzyl)-1,4,5,6,7,8-hexahydro-1,2,6-triaza-azulene;
3-(4-Chloro-phenyl)-1-(3-methyl-benzyl)-1,4,5,6,7,8-hexahydro-1,2,6-triaza-azulene;
3-(4-Chloro-phenyl)-1-(4-fluoro-benzyl)-1,4,5,6,7,8-hexahydro-1,2,6-triaza-azulene;
3-(4-Chloro-phenyl)-1-(3-fluoro-benzyl)-1,4,5,6,7,8-hexahydro-1,2,6-triaza-azulene;
3-(4-Chloro-phenyl)-1-(4-methyl-benzyl)-1,4,5,6,7,8-hexahydro-1,2,6-triaza-azulene;
3-(4-Chloro-phenyl)-1-(3,4-difluoro-benzyl)-1,4,5,6,7,8-hexahydro-1,2,6-triaza-azulene;
3-(4-Chloro-phenyl)-1-(3-nitro-benzyl)-1,4,5,6,7,8-hexahydro-1,2,6-triaza-azulene;
3-(4-Chloro-phenyl)-1-(3-fluoro-4-methyl-benzyl)-1,4,5,6,7,8-hexahydro-1,2,6-triaza-azulene;

3-(4-Chloro-phenyl)-1-(3,4-dimethyl-benzyl)-1,4,5,6,7,8-hexahydro-1,2,6-triaza-azulene;
5-[3-(4-Chloro-phenyl)-5,6,7,8-tetrahydro-4H-1,2,6-triaza-azulen-2-yl]-pentanoic acid methyl ester;
5-[3-(4-Chloro-phenyl)-5,6,7,8-tetrahydro-4H-1,2,6-triaza-azulen-2-yl]-pentan-1-ol;
5-[3-(4-Chloro-phenyl)-5,6,7,8-tetrahydro-4H-1,2,6-triaza-azulen-1-yl]-pentanoic acid methyl ester;
5-[3-(4-Chloro-phenyl)-5,6,7,8-tetrahydro-4H-1,2,6-triaza-azulen-1-yl]-pentan-1-ol;
4-[3-(4-Chloro-phenyl)-5,6,7,8-tetrahydro-4H-1,2,6-triaza-azulen-1-yl]-butyric acid methyl ester;
4-[3-(4-Chloro-phenyl)-5,6,7,8-tetrahydro-4H-1,2,6-triaza-azulen-1-yl]-butan-1-ol;
3-(4-Chloro-phenyl)-2-(3,4-difluoro-benzyl)-2,4,5,6,7,8-hexahydro-1,2,6-triaza-azulene;
3-(4-Chloro-phenyl)-2-(4-methyl-benzyl)-2,4,5,6,7,8-hexahydro-1,2,6-triaza-azulene;
3-(4-Chloro-phenyl)-1-(3-fluoro-4-methoxy-benzyl)-1,4,5,6,7,8-hexahydro-1,2,6-triaza-azulene;
3-(4-Chloro-phenyl)-2-(3-fluoro-4-methoxy-benzyl)-2,4,5,6,7,8-hexahydro-1,2,6-triaza-azulene;
3-(4-Chloro-phenyl)-1-(4-nitro-benzyl)-1,4,5,6,7,8-hexahydro-1,2,6-triaza-azulene;
4-(3-Phenyl-5,6,7,8-tetrahydro-4H-1,2,6-triaza-azulen-1-ylmethyl)-phenylamine;
N-[4-(3-Phenyl-5,6,7,8-tetrahydro-4H-1,2,6-triaza-azulen-1-ylmethyl)-phenyl]-methanesulfonamide;
N,N-[4-(3-phenyl-5,6,7,8-tetrahydro-4H-1,2,6-triaza-azulen-1-ylmethyl)-phenyl]-dimethanesulfonamide;
1-Benzyl-3-p-tolyl-1,4,5,6,7,8-hexahydro-1,2,6-triaza-azulene;
3-(4-Chloro-phenyl)-1-thiophen-2-ylmethyl-1,4,5,6,7,8-hexahydro-1,2,6-triaza-azulene;
1-Benzyl-3-thiophen-2-yl-1,4,5,6,7,8-hexahydro-1,2,6-triaza-azulene;
3-(4-Chloro-phenyl)-1-(3-methoxy-benzyl)-1,4,5,6,7,8-hexahydro-1,2,6-triaza-azulene;
3-(4-Chloro-phenyl)-1-(2-fluoro-benzyl)-1,4,5,6,7,8-hexahydro-1,2,6-triaza-azulene;
3-(4-Chloro-phenyl)-1-(2-methyl-benzyl)-1,4,5,6,7,8-hexahydro-1,2,6-triaza-azulene;
3-(4-Chloro-phenyl)-1-(2,4-difluoro-benzyl)-1,4,5,6,7,8-hexahydro-1,2,6-triaza-azulene;
3-(4-Chloro-phenyl)-1-(2-methoxy-benzyl)-1,4,5,6,7,8-hexahydro-1,2,6-triaza-azulene;
1-(2-Chloro-benzyl)-3-(4-chloro-phenyl)-1,4,5,6,7,8-hexahydro-1,2,6-triaza-azulene;
1-But-3-enyl-3-(4-chloro-phenyl)-1,4,5,6,7,8-hexahydro-1,2,6-triaza-azulene;
1-(2-Bromo-benzyl)-3-(4-chloro-phenyl)-1,4,5,6,7,8-hexahydro-1,2,6-triaza-azulene;
1-(4-Bromo-benzyl)-3-(4-chloro-phenyl)-1,4,5,6,7,8-hexahydro-1,2,6-triaza-azulene;
3-(4-Chloro-phenyl)-1-(2-ethyl-butyl)-1,4,5,6,7,8-hexahydro-1,2,6-triaza-azulene;
3-(4-Chloro-phenyl)-1-(5-chloro-thiophen-2-ylmethyl)-1,4,5,6,7,8-hexahydro-1,2,6-triaza-azulene;
1-(3-Bromo-benzyl)-3-(4-chloro-phenyl)-1,4,5,6,7,8-hexahydro-1,2,6-triaza-azulene;
3-(4-Chloro-phenyl)-1-cyclohexylmethyl-1,4,5,6,7,8-hexahydro-1,2,6-triaza-azulene;
3-(4-Chloro-phenyl)-1-isobutyl-1,4,5,6,7,8-hexahydro-1,2,6-triaza-azulene;
1-Benzo[1,3]dioxol-5-ylmethyl-3-(4-chloro-phenyl)-1,4,5,6,7,8-hexahydro-1,2,6-triaza-azulene;
3-(4-Chloro-phenyl)-1-(tetrahydro-pyran-4-ylmethyl)-1,4,5,6,7,8-hexahydro-1,2,6-triaza-azulene;
3-(4-Chloro-phenyl)-1-(2,6-difluoro-benzyl)-1,4,5,6,7,8-hexahydro-1,2,6-triaza-azulene;
3-(4-Chloro-phenyl)-2-cyclohexylmethyl-2,4,5,6,7,8-hexahydro-1,2,6-triaza-azulene;
3-(4-Chloro-phenyl)-1-(4-methoxy-benzyl)-1,4,5,6,7,8-hexahydro-1,2,6-triaza-azulene;
3-(4-Chloro-phenyl)-1-(3-methyl-butyl)-1,4,5,6,7,8-hexahydro-1,2,6-triaza-azulene;
3-(4-Chloro-phenyl)-1-(2-trifluoromethyl-benzyl)-1,4,5,6,7,8-hexahydro-1,2,6-triaza-azulene;
3-(4-Chloro-phenyl)-2-(2-methyl-benzyl)-2,4,5,6,7,8-hexahydro-1,2,6-triaza-azulene;
2-Benzyl-3-(4-chloro-phenyl)-2,4,5,6,7,8-hexahydro-1,2,6-triaza-azulene;
3-(4-Chloro-phenyl)-1-(4-methoxy-2-methyl-benzyl)-1,4,5,6,7,8-hexahydro-1,2,6-triaza-azulene;
3-(4-Chloro-phenyl)-2-(2,4-difluoro-benzyl)-2,4,5,6,7,8-hexahydro-1,2,6-triaza-azulene;
5-[3-(4-Chloro-phenyl)-5,6,7,8-tetrahydro-4H-1,2,6-triaza-azulen-2-ylmethyl]-furan-2-carboxylic acid ethyl ester;
3-(4-Chloro-phenyl)-2-isobutyl-2,4,5,6,7,8-hexahydro-1,2,6-triaza-azulene;
3-(4-Chloro-phenyl)-2-(2-methoxy-benzyl)-2,4,5,6,7,8-hexahydro-1,2,6-triaza-azulene;
2-Benzyl-3-phenyl-2,4,5,6,7,8-hexahydro-1,2,6-triaza-azulene;
3-(4-Chloro-phenyl)-1-prop-2-ynyl-1,4,5,6,7,8-hexahydro-1,2,6-triaza-azulene;
3-(4-Chloro-phenyl)-1-pentafluorophenylmethyl-1,4,5,6,7,8-hexahydro-1,2,6-triaza-azulene;
3-(4-Chloro-phenyl)-2-thiophen-2-ylmethyl-2,4,5,6,7,8-hexahydro-1,2,6-triaza-azulene;
3-(4-Chloro-phenyl)-1-(2,4,6-trifluoro-benzyl)-1,4,5,6,7,8-hexahydro-1,2,6-triaza-azulene;
2-[3-(4-Chloro-phenyl)-5,6,7,8-tetrahydro-4H-1,2,6-triaza-azulen-1-ylmethyl]-benzonitrile;
3-(4-Chloro-phenyl)-2-(5-chloro-thiophen-2-ylmethyl)-2,4,5,6,7,8-hexahydro-1,2,6-triaza-azulene;
3-(4-Chloro-phenyl)-2-(2,6-difluoro-benzyl)-2,4,5,6,7,8-hexahydro-1,2,6-triaza-azulene;
3-(4-Chloro-phenyl)-2-(2-trifluoromethyl-benzyl)-2,4,5,6,7,8-hexahydro-1,2,6-triaza-azulene;
3-(4-Chloro-phenyl)-1-naphthalen-2-ylmethyl-1,4,5,6,7,8-hexahydro-1,2,6-triaza-azulene;
3-(4-Chloro-phenyl)-2-(2-ethyl-butyl)-2,4,5,6,7,8-hexahydro-1,2,6-triaza-azulene;
3-(4-Chloro-phenyl)-1-naphthalen-1-ylmethyl-1,4,5,6,7,8-hexahydro-1,2,6-triaza-azulene;
2-Benzo[1,3]dioxol-5-ylmethyl-3-(4-chloro-phenyl)-2,4,5,6,7,8-hexahydro-1,2,6-triaza-azulene;
[3-(4-Chloro-phenyl)-5,6,7,8-tetrahydro-4H-1,2,6-triaza-azulen-1-yl]-acetic acid methyl ester;
2-[3-(4-Chloro-phenyl)-5,6,7,8-tetrahydro-4H-1,2,6-triaza-azulen-1-yl]-N-methyl-acetamide;
3-(4-Chloro-phenyl)-2-pentafluorophenylmethyl-2,4,5,6,7,8-hexahydro-1,2,6-triaza-azulene;
3-[3-(4-Chloro-phenyl)-5,6,7,8-tetrahydro-4H-1,2,6-triaza-azulen-1-ylmethyl]-phenol;
4-[3-(4-Chloro-phenyl)-5,6,7,8-tetrahydro-4H-1,2,6-triaza-azulen-1-ylmethyl]-phenol;
4-[3-(4-Chloro-phenyl)-5,6,7,8-tetrahydro-4H-1,2,6-triaza-azulen-1-ylmethyl]-3-methyl-phenol;
4-[3-(4-Chloro-phenyl)-5,6,7,8-tetrahydro-4H-1,2,6-triaza-azulen-1-ylmethyl]-benzene-1,2-diol;

4-[3-(4-Chloro-phenyl)-5,6,7,8-tetrahydro-4H-1,2,6-triaza-azulen-1-ylmethyl]-2-fluoro-phenol;
4-[3-(4-Chloro-phenyl)-5,6,7,8-tetrahydro-4H-1,2,6-triaza-azulen-2-ylmethyl]-2-fluoro phenol;
2-[3-(4-Chloro-phenyl)-5,6,7,8-tetrahydro-4H-1,2,6-triaza-azulen-1-ylmethyl]-phenol;
4-[3-(4-Chloro-phenyl)-5,6,7,8-tetrahydro-4H-1,2,6-triaza-azulen-2-ylmethyl]-3-methyl-phenol;
2-[3-(4-Chloro-phenyl)-5,6,7,8-tetrahydro-4H-1,2,6-triaza-azulen-2-ylmethyl]-phenol;
1-Benzyl-3-(4-chloro-phenyl)-6-methyl-1,4,5,6,7,8-hexahydro-1,2,6-triaza-azulene;
1-Benzyl-3-(4-chloro-phenyl)-6-ethyl-1,4,5,6,7,8-hexahydro-1,2,6-triaza-azulene;
3-(4-Chloro-phenyl)-6-(3,4-dimethoxy-benzyl)-1,4,5,6,7,8-hexahydro-1,2,6-triaza-azulene;
1-Butyl-3-(4-chloro-phenyl)-6-(3,4-dimethoxy-benzyl)-1,4,5,6,7,8-hexahydro-1,2,6-triaza-azulene;
1-Benzyl-3-(4-chloro-phenyl)-6-(3,4-dimethoxy-benzyl)-1,4,5,6,7,8-hexahydro-1,2,6-triaza-azulene;
[1-Benzyl-3-(4-chloro-phenyl)-4,5,7,8-tetrahydro-1H-1,2,6-triaza-azulen-6-yl]-acetic acid methyl ester;
2-[1-Benzyl-3-(4-chloro-phenyl)-4,5,7,8-tetrahydro-1H-1,2,6-triaza-azulen-6-yl]-ethanol;
3-(4-Chloro-phenyl)-1-phenyl-1,4,5,6,7,8-hexahydro-1,2,6-triaza-azulene;
3-(4-Chloro-phenyl)-1-(2-methyl-benzyl)-4,5,6,7,8,9-hexahydro-1H-1,2,6-triaza-cyclopentacyclooctene;
3-(4-Chloro-phenyl)-1-(2-methyl-benzyl)-4,5,6,7,8,9-hexahydro-1H-1,2,7-triaza-cyclopentacyclooctene;
3-(4-Chloro-phenyl)-1-(2-methyl-benzyl)-4,5,6,7-tetrahydro-1H-pyrazolo[3,4-c]pyridine;
2,3-Diphenyl-2,4,5,6,7,8-hexahydro-1,2,6-triaza-azulene;
2-Cyclohexyl-3-phenyl-2,4,5,6,7,8-hexahydro-1,2,6-triaza-azulene;
3-(4-Chloro-phenyl)-2-cyclohexyl-2,4,5,6,7,8-hexahydro-1,2,6-triaza-azulene;
2-Cyclohexyl-3-(4-trifluoromethyl-phenyl)-2,4,5,6,7,8-hexahydro-1,2,6-triaza-azulene;
2-Cyclopentyl-3-phenyl-2,4,5,6,7,8-hexahydro-1,2,6-triaza-azulene;
3-(4-Chloro-phenyl)-2-cyclopentyl-2,4,5,6,7,8-hexahydro-1,2,6-triaza-azulene;
2-Cyclopentyl-3-(4-fluoro-phenyl)-2,4,5,6,7,8-hexahydro-1,2,6-triaza-azulene;
2-(1-Ethyl-propyl)-3-(3-fluoro-phenyl)-2,4,5,6,7,8-hexahydro-1,2,6-triaza-azulene;
2-(1-Ethyl-propyl)-3-(4-fluoro-phenyl)-2,4,5,6,7,8-hexahydro-1,2,6-triaza-azulene;
2-(1-Ethyl-propyl)-3-thiophen-3-yl-2,4,5,6,7,8-hexahydro-1,2,6-triaza-azulene;
2-(1-Ethyl-propyl)-3-phenyl-2,4,5,6,7,8-hexahydro-1,2,6-triaza-azulene;
3-(4-Chloro-phenyl)-2-(2,2,2-trifluoro-ethyl)-2,4,5,6,7,8-hexahydro-1,2,6-triaza-azulene;
2-(2,2,2-Trifluoro-ethyl)-3-(4-trifluoromethyl-phenyl)-2,4,5,6,7,8-hexahydro-1,2,6-triaza-azulene;
2-Isopropyl-3-phenyl-2,4,5,6,7,8-hexahydro-1,2,6-triaza-azulene;
3-(4-Fluoro-phenyl)-2-isopropyl-2,4,5,6,7,8-hexahydro-1,2,6-triaza-azulene;
2-(1-Ethyl-propyl)-3-thiophen-2-yl-2,4,5,6,7,8-hexahydro-1,2,6-triaza-azulene;
2-Cyclopentyl-3-thiophen-3-yl-2,4,5,6,7,8-hexahydro-1,2,6-triaza-azulene;
2-Ethyl-3-phenyl-2,4,5,6,7,8-hexahydro-1,2,6-triaza-azulene;
2-Ethyl-3-(4-fluoro-phenyl)-2,4,5,6,7,8-hexahydro-1,2,6-triaza-azulene;
2-Ethyl-3-thiophen-2-yl-2,4,5,6,7,8-hexahydro-1,2,6-triaza-azulene;
2-(3-Chloro-phenyl)-3-phenyl-2,4,5,6,7,8-hexahydro-1,2,6-triaza-azulene;
2-(3-Fluoro-phenyl)-3-phenyl-2,4,5,6,7,8-hexahydro-1,2,6-triaza-azulene;
2-(2-Chloro-phenyl)-3-phenyl-2,4,5,6,7,8-hexahydro-1,2,6-triaza-azulene;
2-Phenyl-3-thiophen-2-yl-2,4,5,6,7,8-hexahydro-1,2,6-triaza-azulene;
3-(4-Fluoro-phenyl)-2-phenyl-2,4,5,6,7,8-hexahydro-1,2,6-triaza-azulene;
3-(4-Chloro-phenyl)-2-phenyl-2,4,5,6,7,8-hexahydro-1,2,6-triaza-azulene;
3-(3-Chloro-phenyl)-2-phenyl-2,4,5,6,7,8-hexahydro-1,2,6-triaza-azulene;
2-Phenyl-3-p-tolyl-2,4,5,6,7,8-hexahydro-1,2,6-triaza-azulene;
2,3-Diphenyl-4,5,6,7-tetrahydro-2H-pyrazolo[4,3-c]pyridine;
3-Phenyl-2-(3-trifluoromethyl-phenyl)-2,4,5,6,7,8-hexahydro-1,2,6-triaza-azulene;
3-(4-Methoxy-phenyl)-2-phenyl-2,4,5,6,7,8-hexahydro-1,2,6-triaza-azulene;
6-Methyl-2,3-diphenyl-2,4,5,6,7,8-hexahydro-1,2,6-triaza-azulene;
2-Isopropyl-3-p-tolyl-2,4,5,6,7,8-hexahydro-1,2,6-triaza-azulene;
3-(4-Ethyl-phenyl)-2-isopropyl-2,4,5,6,7,8-hexahydro-1,2,6-triaza-azulene;
3-(4-Chloro-phenyl)-2-isopropyl-2,4,5,6,7,8-hexahydro-1,2,6-triaza-azulene;
4-(2-Isopropyl-2,4,5,6,7,8-hexahydro-1,2,6-triaza-azulen-3-yl)-benzonitrile;
2-Isopropyl-3-(4-trifluoromethyl-phenyl)-2,4,5,6,7,8-hexahydro-1,2,6-triaza-azulene;
2-Ethyl-3-p-tolyl-2,4,5,6,7,8-hexahydro-1,2,6-triaza-azulene;
2-tert-Butyl-3-phenyl-2,4,5,6,7,8-hexahydro-1,2,6-triaza-azulene;
2-tert-Butyl-3-(4-fluoro-phenyl)-2,4,5,6,7,8-hexahydro-1,2,6-triaza-azulene;
2-Cyclopentyl-3-p-tolyl-2,4,5,6,7,8-hexahydro-1,2,6-triaza-azulene;
2-Cyclopentyl-3-(4-trifluoromethyl-phenyl)-2,4,5,6,7,8-hexahydro-1,2,6-triaza-azulene;
3-(3-Chloro-phenyl)-2-cyclopentyl-2,4,5,6,7,8-hexahydro-1,2,6-triaza-azulene;
2-Cyclopentyl-3-(4-methoxy-phenyl)-2,4,5,6,7,8-hexahydro-1,2,6-triaza-azulene;
2-(3,3-Dimethyl-cyclopentyl)-3-phenyl-2,4,5,6,7,8-hexahydro-1,2,6-triaza-azulene;
2-(3,3-Dimethyl-cyclopentyl)-3-(4-fluoro-phenyl-2,4,5,6,7,8-hexahydro-1,2,6-triaza-azulene;
2-Cyclohexyl-3-(4-fluoro-phenyl)-2,4,5,6,7,8-hexahydro-1,2,6-triaza-azulene;
2-Cyclohexyl-3-p-tolyl-2,4,5,6,7,8-hexahydro-1,2,6-triaza-azulene;
2-Cyclohexyl-3-(4-methoxy-phenyl)-2,4,5,6,7,8-hexahydro-1,2,6-triaza-azulene;
4-(2-Cyclohexyl-2,4,5,6,7,8-hexahydro-1,2,6-triaza-azulen-3-yl)-benzonitrile;
3-(3-Chloro-phenyl)-2-cyclohexyl-2,4,5,6,7,8-hexahydro-1,2,6-triaza-azulene;

{4-[3-(4-Chloro-phenyl)-5,6,7,8-tetrahydro-4H-1,2,6-triaza-azulen-1-ylmethyl]-phenyl}-methyl-amine;
3-(4-Fluoro-phenyl)-2-isopropyl-4,5,6,7-tetrahydro-2H-pyrazolo[4,3-c]pyridine;
2-Cyclopentyl-3-furan-3-yl-2,4,5,6,7,8-hexahydro-1,2,6-triaza-azulene;
2-Cyclopentyl-3-thiophen-2-yl-2,4,5,6,7,8-hexahydro-1,2,6-triaza-azulene;
2-tert-Butyl-3-thiophen-3-yl-2,4,5,6,7,8-hexahydro-1,2,6-triaza-azulene;
2-tert-Butyl-3-furan-3-yl-2,4,5,6,7,8-hexahydro-1,2,6-triaza-azulene;
2-Cyclopentyl-3-(3,4-difluoro-phenyl)-2,4,5,6,7,8-hexahydro-1,2,6-triaza-azulene;
3-(4-Chloro-phenyl)-1-cyclobutyl-1,4,5,6,7,8-hexahydro-1,2,6-triaza-azulene;
3-(4-Chloro-phenyl)-2-cyclobutyl-2,4,5,6,7,8-hexahydro-1,2,6-triaza-azulene;
3-(4-Chloro-phenyl)-1-cyclohexyl-1,4,5,6,7,8-hexahydro-1,2,6-triaza-azulene;
2-tert-Butyl-3-thiophen-2-yl-2,4,5,6,7,8-hexahydro-1,2,6-triaza-azulene;
3-(3-Chloro-4-fluoro-phenyl)-2-cyclopentyl-2,4,5,6,7,8-hexahydro-1,2,6-triaza-azulene;
2-Isopropyl-3-(4-methoxy-phenyl)-2,4,5,6,7,8-hexahydro-1,2,6-triaza-azulene;
2-Isopropyl-3-(4-isopropyl-phenyl)-2,4,5,6,7,8-hexahydro-1,2,6-triaza-azulene;
2-Isopropyl-3-m-tolyl-2,4,5,6,7,8-hexahydro-1,2,6-triaza-azulene;
2-Isopropyl-3-o-tolyl-2,4,5,6,7,8-hexahydro-1,2,6-triaza-azulene;
2-Isopropyl-3-thiophen-2-yl-2,4,5,6,7,8-hexahydro-1,2,6-triaza-azulene;
3-(2-Chloro-phenyl)-2-isopropyl-2,4,5,6,7,8-hexahydro-1,2,6-triaza-azulene;
2-Isopropyl-3-(4-nitro-phenyl)-2,4,5,6,7,8-hexahydro-1,2,6-triaza-azulene;
3-(4-Chloro-phenyl)-1-cycloheptyl-1,4,5,6,7,8-hexahydro-1,2,6-triaza-azulene;
3-(4-Chloro-phenyl)-1-cyclooctyl-1,4,5,6,7,8-hexahydro-1,2,6-triaza-azulene;
2-Ethyl-3-(4-ethyl-phenyl)-2,4,5,6,7,8-hexahydro-1,2,6-triaza-azulene;
4-(2-Ethyl-2,4,5,6,7,8-hexahydro-1,2,6-triaza-azulen-3-yl)-benzonitrile;
3-(4-Fluoro-phenyl)-2-isopropyl-6-methyl-2,4,5,6,7,8-hexahydro-1,2,6-triaza-azulene;
3-(4-Fluoro-phenyl)-2,6-diisopropyl-2,4,5,6,7,8-hexahydro-1,2,6-triaza-azulene;
2-Ethyl-3-(4-isopropyl-phenyl)-2,4,5,6,7,8-hexahydro-1,2,6-triaza-azulene;
2-Ethyl-3-(4-methoxy-phenyl)-2,4,5,6,7,8-hexahydro-1,2,6-triaza-azulene;
2-Ethyl-3-(4-trifluoromethyl-phenyl)-2,4,5,6,7,8-hexahydro-1,2,6-triaza-azulene;
2-Ethyl-3-o-tolyl-2,4,5,6,7,8-hexahydro-1,2,6-triaza-azulene;
3-(2-Chloro-phenyl)-2-ethyl-2,4,5,6,7,8-hexahydro-1,2,6-triaza-azulene;
2-Ethyl-3-(2-fluoro-phenyl)-2,4,5,6,7,8-hexahydro-1,2,6-triaza-azulene;
3-(2,4-Dichloro-phenyl)-2-isopropyl-2,4,5,6,7,8-hexahydro-1,2,6-triaza-azulene;
6-Benzyl-3-(4-fluoro-phenyl)-2-isopropyl-2,4,5,6,7,8-hexahydro-1,2,6-triaza-azulene;
3-(4-Fluoro-phenyl)-2-isopropyl-6-(3-phenyl-propyl)-2,4,5,6,7,8-hexahydro-1,2,6-triaza-azulene;
3-(4-Fluoro-phenyl)-2-isopropyl-6-phenethyl-2,4,5,6,7,8-hexahydro-1,2,6-triaza-azulene;
1-Benzyl-3-(4-chloro-phenyl)-1,4,5,6,7,8-hexahydro-1,2,6-triaza-azulene citrate salt;
2-Cyclobutyl-3-phenyl-2,4,5,6,7,8-hexahydro-1,2,6-triaza-azulene;
2-Cyclobutyl-3-(4-fluoro-phenyl)-2,4,5,6,7,8-hexahydro-1,2,6-triaza-azulene;
2-Cyclobutyl-3-p-tolyl-2,4,5,6,7,8-hexahydro-1,2,6-triaza-azulene;
2-Cyclobutyl-3-(4-trifluoromethyl-phenyl)-2,4,5,6,7,8-hexahydro-1,2,6-triaza-azulene;
2-Cyclopropyl-3-(4-fluoro-phenyl)-2,4,5,6,7,8-hexahydro-1,2,6-triaza-azulene;
2-Cyclopropyl-3-p-tolyl-2,4,5,6,7,8-hexahydro-1,2,6-triaza-azulene;
2-Cyclopropyl-3-thiophen-3-yl-2,4,5,6,7,8-hexahydro-1,2,6-triaza-azulene;
4-(2-Cyclopropyl-2,4,5,6,7,8-hexahydro-1,2,6-triaza-azulen-3-yl)-benzonitrile;
6-Benzyl-2-isopropyl-3-phenyl-4,5,6,7-tetrahydro-2H-pyrazolo[3,4-c]pyridine;
2-Isopropyl-3-phenyl-4,5,6,7-tetrahydro-2H-pyrazolo[3,4-c]pyridine;
6-Benzyl-2-isopropyl-3-thiophen-3-yl-4,5,6,7-tetrahydro-2H-pyrazolo[3,4-c]pyridine;
6-Benzyl-2-isopropyl-3-p-tolyl-4,5,6,7-tetrahydro-2H-pyrazolo[3,4-c]pyridine.
6-Benzyl-3-(4-fluoro-phenyl)-2-isopropyl-4,5,6,7-tetrahydro-2H-pyrazolo[3,4-c]pyridine;
3-(4-Fluoro-phenyl)-2-isopropyl-4,5,6,7-tetrahydro-2H-pyrazolo[3,4-c]pyridine;
2-Isopropyl-3-p-tolyl-4,5,6,7-tetrahydro-2H-pyrazolo[3,4-c]pyridine;
2-sec-Butyl-3-phenyl-2,4,5,6,7,8-hexahydro-1,2,6-triaza-azulene;
2-sec-Butyl-3-(4-fluoro-phenyl)-2,4,5,6,7,8-hexahydro-1,2,6-triaza-azulene;
2-sec-Butyl-3-p-tolyl-2,4,5,6,7,8-hexahydro-1,2,6-triaza-azulene;
2-sec-Butyl-3-(4-trifluoromethyl-phenyl)-2,4,5,6,7,8-hexahydro-1,2,6-triaza-azulene;
2-Cyclopentyl-3-(4-fluoro-phenyl)-6-methyl-2,4,5,6,7,8-hexahydro-1,2,6-triaza-azulene;
6-Benzyl-3-(4-fluoro-phenyl)-2-isopropyl-8-methyl-2,4,5,6,7,8-hexahydro-1,2,6-triaza-azulene;
3-(4-Fluoro-phenyl)-2-isopropyl-8-methyl-2,4,5,6,7,8-hexahydro-1,2,6-triaza-azulene;
3-(4-Fluoro-phenyl)-2-isopropyl-4-methyl-2,4,5,6,7,8-hexahydro-1,2,6-triaza-azulene;
2-Cyclopentyl-3-(4-fluoro-phenyl)-5-methyl-2,4,5,6,7,8-hexahydro-1,2,6-triaza-azulene;
2-Cyclopentyl-7-methyl-3-p-tolyl-2,4,5,6,7,8-hexahydro-1,2,6-triaza-azulene;
2-Isopropyl-7-methyl-3-phenyl-2,4,5,6,7,8-hexahydro-1,2,6-triaza-azulene;
2-Isopropyl-5-methyl-3-phenyl-2,4,5,6,7,8-hexahydro-1,2,6-triaza-azulene;
3-(4-Fluoro-phenyl)-2-isopropyl-7-methyl-2,4,5,6,7,8-hexahydro-1,2,6-triaza-azulene;
3-(4-Fluoro-phenyl)-2-isopropyl-5-methyl-2,4,5,6,7,8-hexahydro-1,2,6-triaza-azulene;
2-Isopropyl-7-methyl-3-p-tolyl-2,4,5,6,7,8-hexahydro-1,2,6-triaza-azulene;

3-(4-Chloro-phenyl)-1-pyridin-4-ylmethyl-1,4,5,6,7,8-hexahydro-1,2,6-triaza-azulene;
3-(4-Chloro-phenyl)-pyridin-2-ylmethyl-1,4,5,6,7,8-hexahydro-1,2,6-triaza-azulene;
3-(4-Chloro-phenyl)-1-pyridin-3-ylmethyl-1,4,5,6,7,8-hexahydro-1,2,6-triaza-azulene;
3-(4-Chloro-phenyl)-1-(tetrahydro-pyran-4-yl)-1,4,5,6,7,8-hexahydro-1,2,6-triaza-azulene;
3-(4-Chloro-phenyl)-1-(4-methyl-cyclohexyl)-1,4,5,6,7,8-hexahydro-1,2,6-triaza-azulene;
{2-[3-(4-Chloro-phenyl)-5,6,7,8-tetrahydro-4H-1,2,6-triaza-azulen-1-yl]-ethyl}-dimethyl-amine.
2-[1-Benzyl-3-(4-chloro-phenyl)-4,5,7,8-tetrahydro-1H-1,2,6-triaza-azulen-6-yl]-acetamide;
3-[3-(4-Chloro-phenyl)-5,6,7,8-tetrahydro-4H-1,2,6-triaza-azulen-1-yl]-propionitrile;
3-[3-(4-Chloro-phenyl)-5,6,7,8-tetrahydro-4H-1,2,6-triaza-azulen-2-yl]-propionitrile;
3-(4-Chloro-phenyl)-2-cycloheptyl-2,4,5,6,7,8-hexahydro-1,2,6-triaza-azulene;
1-(4-Chloro-benzyl)-3-(4-chloro-phenyl)-1,4,5,6,7,8-hexahydro-1,2,5-triaza-azulene;
3-(4-Chloro-phenyl)-1-(3,4-difluoro-benzyl)-1,4,5,6,7,8-hexahydro-1,2,5-triaza-azulene;
3-(4-Chloro-phenyl)-1-(3-methyl-benzyl)-1,4,5,6,7,8-hexahydro-1,2,5-triaza-azulene;
3-(4-Chloro-phenyl)-1-(4-fluoro-3-methyl-benzyl)-1,4,5,6,7,8-hexahydro-1,2,5-triaza-azulene;
3-(4-Fluoro-phenyl)-2-isopropyl-2,4,5,6,7,8-hexahydro-1,2,6-triaza-azulene citrate salt; and
2-Cyclopentyl-3-(4-fluoro-phenyl)-2,4,5,6,7,8-hexahydro-1,2,6-triaza-azulene citrate salt.

In other preferred embodiments, the 5-HT7 receptor antagonist is selected from compounds of the following Formulae (I) or (II):

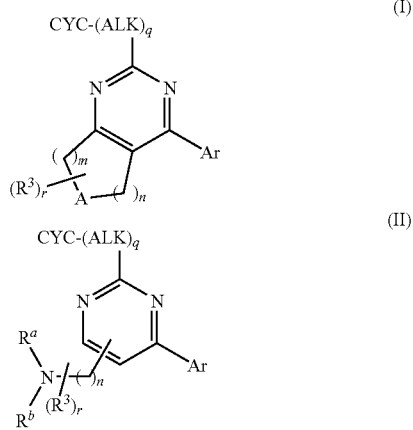

wherein
m is 1, 2, or 3;
n is 1, 2, or 3;
where when m and n are both present, m+n is greater than or equal to 2, and is less than or equal to 4;
$R^a$ and $R^b$ are each independently —H, —$C_{1-7}$alkyl, or —$C_{3-7}$cycloalkyl, or $R^a$ and $R^b$ taken together with the nitrogen of attachment form piperidinyl, pyrrolidinyl, morpholinyl, thiomorpholinyl, or piperazinyl, where each $R^a$ and $R^b$ is optionally and independently substituted with —$C_{1-4}$alkyl;

q is 0 or 1;
A is >$NR^1$, >$CHNR^cR^d$, >CHOH, or —$CH_2$—, wherein
 $R^1$ is selected from the group consisting of —H, —$C_{1-7}$alkyl, —$C_{3-7}$cycloalkyl, and benzyl, where each alkyl, cycloalkyl, or benzyl is optionally mono-, di-, or tri-substituted with $R^e$;
 $R^e$ is selected from the group consisting of —$C_{1-4}$alkyl, —$C_{2-4}$alkenyl, —$C_{2-4}$alkynyl, —$C_{3-6}$cycloalkyl, halo, —$CF_3$, —OH, —$OC_{1-4}$alkyl, —$OCF_3$, —N($R^f$)$R^g$ (wherein $R^f$ and $R^g$ are independently —H or —$C_{1-4}$alkyl, or $R^f$ and $R^g$ taken together with the nitrogen of attachment form piperidinyl, pyrrolidinyl, morpholinyl, thiomorpholinyl, or piperazinyl), —C(O)N($R^f$)$R^g$, —N($R^h$)C(O)$R^h$, —N($R^h$)$SO_2C_{1-7}$alkyl (wherein $R^h$ is —H or —$C_{1-4}$alkyl, or two $R^h$ in the same substituent taken together with the amide of attachment form an otherwise aliphatic 4- to 6-membered ring), —S(O)$_{0-2}$—$C_{1-4}$alkyl, —$SO_2$N($R^f$)$R^g$, —$SCF_3$, —C(O)$C_{1-4}$alkyl, —CN, —COOH, and —COO$C_{1-4}$alkyl;
 $R^c$ and $R^d$ are independently selected from the group consisting of —H, —$C_{1-7}$alkyl, —$C_{3-7}$alkenyl, —$C_{3-7}$alkynyl, —$C_{3-7}$cycloalkyl, —$C_{1-7}$alkyl $C_{3-7}$cycloalkyl, and —$C_{3-7}$cycloalkyl $C_{1-7}$alkyl, or $R^c$ and $R^d$ taken together with the nitrogen of attachment form piperidinyl, pyrrolidinyl, morpholinyl, thiomorpholinyl, or piperazinyl, where each $R^c$ and $R^d$ is optionally and independently substituted with $R^e$;
$R^3$ is —$C_{1-4}$alkyl, —$C_{1-4}$alkenyl, or benzyl, each optionally substituted with —$C_{1-3}$alkyl, —OH, or halo, or two $R^3$ substituents taken together form $C_{2-5}$alkylene optionally substituted with —$C_{1-3}$alkyl, —OH, or halo;
r is 0 or is an integer less than or equal to m+n+1;
Ar is an aryl or heteroaryl ring selected from the group consisting of:
 a) phenyl, optionally mono-, di-, or tri-substituted with $R^i$ or di-substituted on adjacent carbons with —$OC_{1-4}$alkyleneO-, —$(CH_2)_{2-3}$NH—, —$(CH_2)_{1-2}$NH($CH_2$)—, —$(CH_2)_{2-3}$N($C_{1-4}$alkyl)-, or —$(CH_2)_{1-2}$N($C_{1-4}$alkyl)($CH_2$)—;
  $R^i$ is selected from the group consisting of —$C_{1-7}$alkyl, —$C_{2-7}$alkenyl, —$C_{2-7}$alkynyl, —$C_{3-7}$cycloalkyl, halo, —$CF_3$, —OH, —$OC_{1-7}$alkyl, —$OCF_3$, —$OC_{3-7}$alkenyl, —$OC_{3-7}$alkynyl, —N($R^j$)$R^k$ (wherein $R^j$ and $R^k$ are independently —H or —$C_{1-4}$alkyl), —C(O)N($R^j$)$R^k$, —N($R^j$)C(O)$R^k$, —N($R^j$)$SO_2C_{1-6}$alkyl, —S(O)$_{0-2}$—$C_{1-6}$alkyl, —$SO_2$N($R^j$)$R^k$, —$SCF_3$, —C(O)$C_{1-6}$alkyl, —$NO_2$, —CN, —COOH, and —COO$C_{1-7}$alkyl;
 b) a monocyclic aromatic hydrocarbon group having five ring atoms, having a carbon atom which is the point of attachment, having one carbon atom replaced by >O, >S, >NH, or >N($C_{1-4}$alkyl), having up to two additional carbon atoms optionally replaced by —N=, optionally mono- or di-substituted with $R^i$;
 c) a monocyclic aromatic hydrocarbon group having six ring atoms, having a carbon atom which is the point of attachment, having one or two carbon atoms replaced by —N=, optionally mono- or di-substituted with $R^i$; and
 d) phenyl or pyridyl, substituted with a substituent selected from the group consisting of phenyl, phenoxy, pyridyl, thiophenyl, oxazolyl, and tetrazolyl, where the resultant substituted moiety is optionally further mono-, di-, or tri-substituted with $R^i$;

ALK is a branched or unbranched $C_{1-7}$alkylene, $C_{2-7}$alkenylene, $C_{2-7}$alkynylene, $C_{3-7}$cycloalkylene, or $C_{3-7}$cycloalkenylene, optionally mono-, di-, or tri-substituted with $R^m$;

$R^m$ is selected from the group consisting of halo, —$CF_3$, —OH, —$OC_{1-7}$alkyl, —$OC_{3-7}$cycloalkyl, —$OCF_3$, —$N(R^p)R^s$ (wherein $R^p$ and $R^s$ are independently —H or —$C_{1-7}$alkyl), —$C(O)N(R^p)R^s$, —$N(R^t)C(O)R^t$, —$N(R^t)SO_2C_{1-6}$alkyl (wherein $R^t$ is —H or —$C_{1-7}$alkyl), —$S(O)_{0-2}$—$C_{1-6}$alkyl, —$SO_2N(R^p)R^s$, —$SCF_3$, —CN, —$NO_2$, —$C(O)C_{1-7}$alkyl, —COOH, and —$COOC_{1-7}$alkyl;

CYC is —H or is a ring system selected from the group consisting of:
  i) phenyl, optionally mono-, di-, or tri-substituted with $R^u$ or di-substituted on adjacent carbons with —$OC_{1-4}$alkyleneO—, —$(CH_2)_{2-3}NH$—, —$(CH_2)_{1-2}NH(CH_2)$—, —$(CH_2)_{2-3}N(C_{1-4}alkyl)$-, or —$(CH_2)_{1-2}N(C_{1-4}alkyl)(CH_2)$—;

$R^u$ is selected from the group consisting of —$C_{1-7}$alkyl, —$C_{3-7}$cycloalkyl, phenyl, benzyl, halo, —$CF_3$, —OH, —$OC_{1-7}$alkyl, —$OC_{3-7}$cycloalkyl, -Ophenyl, -Obenzyl, —$OCF_3$, —$N(R^v)R^w$ (wherein $R^v$ and $R^w$ are independently —H or —$C_{1-7}$alkyl, or $R^v$ and $R^w$ taken together with the nitrogen of attachment form piperidinyl, pyrrolidinyl, morpholinyl, thiomorpholinyl, or piperazinyl, where each $R^v$ and $R^w$ is optionally and independently substituted with —OH or —$C_{1-7}$alkyl), —$C(O)N(R^v)R^w$, —$N(R^x)C(O)R^x$, —$N(R^x)SO_2C_{1-6}$alkyl (wherein $R^x$ is —H or —$C_{1-7}$alkyl, or two $R^x$ in the same substituent taken together with the amide of attachment form an otherwise aliphatic 4- to 6-membered ring), —$N(SO_2C_{1-6}alkyl)_2$, —$S(O)_{0-2}$—$C_{1-6}$alkyl, —$SO_2N(R^v)R^w$, —$SCF_3$, —$C(O)C_{1-6}$alkyl, —$NO_2$, —CN, —COOH, and —$COOC_{1-7}$alkyl;

ii) a monocyclic aromatic hydrocarbon group having five ring atoms, having a carbon atom which is the point of attachment, having one carbon atom replaced by >O, >S, >NH, or >$N(C_{1-4}alkyl)$, having up to one additional carbon atoms optionally replaced by —N=, optionally mono- or di-substituted with $R^u$;

iii) a monocyclic aromatic hydrocarbon group having six ring atoms, having a carbon atom which is the point of attachment, having one or two carbon atoms replaced by —N=, optionally mono- or di-substituted with $R^u$; and iv) a non-aromatic heterocyclic ring having 4 to 8 members, said ring having 0, 1, or 2 non-adjacent heteroatom members selected from the group consisting of O, S, —N=, >NH, and >$N(C_{1-4}alkyl)$, having 0, 1, or 2 double bonds, having 0, 1, or 2 carbon members which is a carbonyl, optionally having one carbon member which forms a bridge, having 0 to 5 substituents $R^u$, and where when q is 0, said ring has a carbon atom which is the point of attachment;

and where when the compound is of Formula (I):
  (a) when ALK is methylene, ethylene, propylene, or isopropylene, CYC is —H, Ar is phenyl or mono-substituted phenyl, m is 2, n is 1, and A is >$NR^1$, then $R^1$ is not —$C_{1-4}$alkyl or benzyl;
  (b) when q is 0, CYC is phenyl, Ar is phenyl or 3-chlorophenyl, m is 2, and n is 1, then A is not unsubstituted —$CH_2$—; and
  (c) when q is 0, CYC is 2-pyridyl, Ar is 2-pyridyl, m is 2, and n is 1, then A is not unsubstituted —$CH_2$—;

and enantiomers, diastereomers, hydrates, solvates, and pharmaceutically acceptable salts, esters and amides of such compounds.

Further preferred 5-HT7 receptor antagonists include those described in U.S. patent application Ser. No. 11/460,294, filed Jul. 27, 2006 having an activity ($K_i$) against the 5-HT7 receptor≤1000 nM. Especially preferred 5-HT7 receptor antagonists are the compounds listed below and their pharmaceutically acceptable salts (where a free acid or base is listed) or free acid/base form (where a salt is listed):

2-tert-Butyl-4-(4-fluoro-phenyl)-5,6,7,8-tetrahydro-pyrido[4,3-d]pyrimidine;
2-Cyclopentyl-4-p-tolyl-5,6,7,8-tetrahydro-pyrido[4,3-d]pyrimidine;
2-Isobutyl-4-thiophen-2-yl-5,6,7,8-tetrahydro-pyrido[4,3-d]pyrimidine;
2-Cyclopentyl-4-(4-fluoro-phenyl)-6,7,8,9-tetrahydro-5H-pyrimido[4,5-d]azepine;
2-Cyclopentyl-4-p-tolyl-6,7,8,9-tetrahydro-5H-pyrimido[4,5-d]azepine;
2-Cyclopentyl-4-(4-methoxy-phenyl)-6,7,8,9-tetrahydro-5H-pyrimido[4,5-d]azepine;
4-(2-Cyclopentyl-6,7,8,9-tetrahydro-5H-pyrimido[4,5-d]azepin-4-yl)-benzonitrile;
4-(4-Fluoro-phenyl)-2-isopropyl-6,7,8,9-tetrahydro-5H-pyrimido[4,5-d]azepine hydrochloride;
2-Benzyl-4-p-tolyl-6,7,8,9-tetrahydro-5H-pyrimido[4,5-d]azepine;
2-Benzyl-4-(4-trifluoromethyl-phenyl)-6,7,8,9-tetrahydro-5H-pyrimido[4,5-d]azepine;
2-(4-Fluoro-benzyl)-4-(4-fluoro-phenyl)-6,7,8,9-tetrahydro-5H-pyrimido[4,5-d]azepine;
2-Cyclopentyl-7-methyl-4-p-tolyl-6,7,8,9-tetrahydro-5H-pyrimido[4,5-d]azepine;
2-Cyclopentyl-4-(4-methoxy-phenyl)-7-methyl-6,7,8,9-tetrahydro-5H-pyrimido[4,5-d]azepine;
2-Benzyl-7-methyl-4-p-tolyl-6,7,8,9-tetrahydro-5H-pyrimido[4,5-d]azepine;
2-Isopropyl-4-p-tolyl-6,7,8,9-tetrahydro-5H-pyrimido[4,5-c]azepine hydrochloride;
2-Benzyl-4-(4-fluoro-phenyl)-5,6,7,8-tetrahydro-pyrido[3,4-d]pyrimidine hydrochloride;
2-Benzyl-4-p-tolyl-5,6,7,8-tetrahydro-pyrido[3,4-d]pyrimidine hydrochloride;
2-Benzyl-4-phenyl-5,6,7,8-tetrahydro-pyrido[3,4-d]pyrimidine;
2-Benzyl-4-(4-methoxy-phenyl)-5,6,7,8-tetrahydro-pyrido[3,4-d]pyrimidine;
2-Isopropyl-4-(5-methyl-thiophen-3-yl)-5,6,7,8-tetrahydro-pyrido[3,4-d]pyrimidine hydrochloride; and
{2-[2-tert-Butyl-6-(4-fluoro-phenyl)-pyrimidin-4-yl]-ethyl}-dimethyl-amine.

Additional preferred 5-HT7 antagonist compounds include:
(R)-3-[2-[2-(4-Methylpiperidin-1-yl)ethyl]pyrrolidine-1-sulfonyl]phenol (SB269970);
(R)-3,N-Dimethyl-N-[1-methyl-3-(4-methylpiperidin-1-yl)propyl]benzene sulfonamide (SB258719);
R-(+)-1-(toluene-3-sulfonyl)-2-[2-(4-methylpiperidin-1-yl)ethyl]-pyrrolidine; (SB258741);
LY-215840;
2a-[4-4-phenyl-1,2,3,6-tetrahydropyridyl])-2a,3,4,5-tetrahydrobenzo[ed]-indol[(1H)-1 (DR 4004);
Ensaculin (Schwabe);
S 23751 (Servier/Universite D'Orleans);

Zopetine (Fujisawa/Knoll/Klinge Pharma GmbH); SB248709 (GlaxoSmithKline); and BTS 79018 (Knoll/Abbott).

Preferably, 5-HT7 receptor antagonists are those that possess activity against the 5-HT7 receptor of less than or equal to 100 nM.

Exemplary SRIs that may be used in the methods and compositions of the invention are selected from the various compounds known in the art having SRI activity or as suitably modulating the activity of the serotonin transporter (SERT) receptor, such as those generically or specifically described in described in: International Publication Nos. WO 2006/016262, WO 2005/056056, WO 2005/030132, and WO 01/41766; U.S. Pat. Nos. 4,536,518, 4,314,081, 4,136,193, and 4,007,196; US Patent Application Publication No. 2005/0288355; U.S. patent application Ser. No. 11/424,751, filed Jun. 16, 2006, application Ser. No. 11/424,734, filed Jun. 16, 2006, and application Ser. No. 11/300,880, filed Dec. 15, 2005; and U.S. Provisional Application Nos. 60/806,169, filed Jun. 29, 2006, 60/806,167, filed Jun. 29, 2006, and 60/806,165, filed Jun. 29, 2006; the disclosures of which are incorporated by reference herein. Especially preferred SRIs include SSRIs such as dapoxetine, 1-(3-dimethylaminopropyl)-1-(4-fluorophenyl)-1,3-dihydroisobenzofuran-5-carbonitrile (citalopram), escitalopram, N-methyl-3-phenyl-3-[4-(trifluoromethyl)phenoxy]-propan-1-amine (fluoxetine), fluvoxamine, (1S)-cis-4-(3,4-dichlorophenyl)-1,2,3,4-tetrahydro-N-methyl-1-naphthalenamine (sertraline), (3S-trans)-3-((1,3-Benzodioxol-5-yloxy)methyl)-4-(4-fluorophenyl)-piperidine (paroxetine), venlafaxine, vilazodone, duloxetine, nefazodone, imipramine, femoxetine, clomipramine, cericlamine, clovoxamine, cyanodothiepin, ifoxetine, indalpine, indeloxazine, litoxetine, milnacipran, tametraline, viqualine, and zimeldine, and their pharmaceutically acceptable salts. In one particularly preferred embodiment, the SRI is citalopram, sertraline, paroxetine, fluoxetine, or dapoxetine, or a pharmaceutically acceptable salt thereof.

A "pharmaceutically acceptable salt" is intended to mean a salt of a free acid or base compound that is non-toxic, biologically tolerable, or otherwise biologically suitable for administration to the subject. See, generally, Berge, et al., "Pharmaceutical Salts", *J. Pharm. Sci.,* 1977, 66:1-19. Exemplary pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Although the 5-HT7 receptor antagonist agent and an SRI agent used in accordance with the invention are preferably selective for or specific to a 5-HT7 receptor or a SERT, respectively, either one or both of the agents may also bind to or inhibit another receptor. Thus, one or more of the 5-HT7 receptor antagonist agents or SRI agents may be dual inhibitors. For example, a dual 5-HT2 receptor antagonist/5-HT7 receptor antagonist (see, e.g., US Patent Application Publication No. US 2005/0119295 and International Publication No. WO 2005/040169) may be used in combination with an SRI. Similarly, a suitable dual histamine H3 receptor/SERT inhibitor or SRI (see, e.g., International Publication No. WO 2006/066197, U.S. patent application Ser. No. 11/300,880, filed Dec. 15, 2005, application Ser. No. 11/424,734, filed Jun. 16, 2006, and application Ser. No. 11/424,751, filed Jun. 16, 2006, International Patent Application No. PCT/US2006/023552, filed Jun. 12, 2006, and U.S. Provisional Patent Application Nos. 60/806,165, filed Jun. 29, 2006, 60/806,167, filed Jun. 29, 2006, and 60/806,169, filed Jun. 29, 2006, may be used in combination with a 5-HT7 receptor antagonist.

The present invention also relates to pharmaceutical compositions for treating a serotonin-mediated disease or condition comprising: a) an amount of a 5-HT7 receptor antagonist and an amount of an SRI; and b) a pharmaceutically acceptable excipient. In preferred embodiments, the amount of the 5-HT7 receptor antagonist is a potentiating or ameliorative amount. In further preferred embodiments, the amount of the SRI is a potentiating or ameliorative amount. In a particularly preferred embodiment, the composition comprises an effective amount of an SSRI, preferably citalopram, and an ameliorative amount of a 5-HT7 receptor antagonist sufficient to ameliorate the sleep-fragmentation induction effect of the SSRI.

Optionally, the 5-HT7 receptor antagonist and SRI may be combined with additional active ingredients. The additional active ingredients may be co-administered separately with the 5-HT7 receptor antagonist and SRI agents of the invention (i.e., each in its own unit dosage form), or one or more of the active ingredients may be delivered together in a single composition or unit dosage form containing the agents in a pharmaceutical composition according to the invention.

In one embodiment, the 5-HT7 receptor antagonist and SRI are coadministered in separate pharmaceutical formulations. In a preferred embodiment, the two agents are formulated together into a single pharmaceutical composition. In such pharmaceutical compositions of the invention, the 5-HT7 receptor antagonist and SRI, with optional active ingredients, are combined. In a general aspect, a pharmaceutical composition of the invention therefore comprises: an effective or complementary amount of at least one 5-HT7 receptor antagonist agent and an effective or complementary amount of at least one SRI agent, such amounts of agents together providing an effective combined amount; along with a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation. Additionally, dosage forms may be prepared as immediate-, timed-, controlled-, or extended-release formulations.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds can be delivered separately or together in the form of tablets or capsules, or as a solution, emulsion, or suspension. Oral tablets may include one or both of the agents and any other active ingredients mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

The combination of 5-HT7 receptor antagonist and SRI agents may alternatively be administered by inhalation, via nasal or oral route, e.g., in a spray formulation also containing a suitable carrier.

Various formulations for delivering the combination of 5-HT7 receptor antagonist and SRI in accordance with the invention, either in separate compositions or a single composition, may be routinely developed in view of guidance in the art. See, e.g., U.S. Pat. Nos. 4,576,604, 4,673,405, 4,857,330, 5,997,905, and 6,149,943; US Patent Application Publication No. 2005/0232986; and International Publication Nos. WO 2003/035070 and WO 2000/032173.

Certain aspects, features, or advantages of the invention or exemplary or preferred embodiments are illustrated by the following examples.

EXAMPLES

Animals. All studies involving live animals were carried out in accordance with the Guide for the Care and Use of Laboratory Animals as adopted and promulgated by the US National Institutes of Health. Tail suspension test and locomotor activity measurements were performed in male C57BL/6J mice (Jackson Laboratories) weighing 22-30 grams. Microdialysis blood brain barrier penetration and EEG/EMG experiments were performed in male Sprague-Dawley rats (Charles River, Wilmington, Mass.) weighing 280-320 grams (microdialysis) or 400-500 grams (EEG/EMG). Animals were allowed to acclimate for at least seven days after receipt before experiments were performed. Animals were group-housed in accordance with institutional standards, provided food and water ad libitum, and were maintained on a 12-hour light dark (cycle (lights on: 6:00 to 18:00).

Agents. (R)-3-[2-[2-(4-Methylpiperidin-1-yl)ethyl]pyrrolidine-1-sulfonyl]phenol hydrochloride (SB269970) and 1-(3-dimethylaminopropyl)-1-(4-fluorophenyl)-1,3-dihydroisobenzofuran-5-carbonitrile, HBr salt (citalopram) were purchased from Sigma (Saint Louis, Mo.). 1-Benzyl-3-(4-chloro-phenyl)-1,4,5,6,7,8-hexahydro-1,2,6-triaza-azulene (Compound A) was prepared (see WO 2005/040169 and U.S. Patent Application Publication No. US 2005/0119295). Doses of agents are expressed as their free base.

Tail suspension test. SB269970, citalopram, Compound A, co-administration of SB269970 and citalopram, or co-administration of Compound A and citalopram were each tested at the intraperitoneal (i.p.) doses described below and in the figures. A vehicle control (5% dextrose) and a positive control (citalopram, 5 mg/kg i.p.) were included in experiments indicated. All compounds were formulated in 5% dextrose. Dilutions of compound stock solutions were prepared with vehicle. All doses were randomized and administered at 10 mL/kg, i.p. Mice were dosed thirty minutes prior to testing. Mice were prepared for use in tail suspension tests by adhering a piece of tape to the upper middle of each animal's tail, creating a flap with the overlap of tape. One strand of a size 0 polyester suture with an attached needle was tied to a previously calibrated force transducer (AD Instruments MLT500/D). The needle end of the suture hung down from the force transducer, and was inserted through the tape flap of each animal. All mice were hung face-down from the force transducer in this manner for six minutes. During testing a Power Lab (AD Instruments, Colorado Springs, Colo.) recorded the data from the force transducer via a bridge amplifier. The data were accessible using Chart 4 software (AD Instruments, Colorado Springs, Colo.). Time spent struggling and time spent immobile were differentiated by hand-scoring of the force-versus-time trace using the Chart 4 software. The time spent immobile was totaled for the last four minutes of the six-minute test for each animal, averaged for each dose group, and then compared. Data were graphed and statistics were calculated using Prism software (GraphPad, San Diego, Calif.). Data are presented as the mean±SEM and evaluated by one-way analysis of variance followed by Bonferroni's multiple comparison test. Differences were considered significant at $p<0.05$ Locomotor activity. SB269970 (10 mg/kg i.p.), citalopram (1 mg/kg i.p.), Compound A (1 mg/kg i.p.), co-administration of SB269970 (10 mg/kg i.p.) and citalopram (1 mg/kg i.p.), or co-administration Compound A (1 mg/kg i.p.) and citalopram (1 mg/kg i.p.) were tested. Drugs were formulated in 5% dextrose. Animals in the vehicle group were injected with 5% dextrose. Locomotor activity was measured with the Motor-Monitor System (Hamilton Kinder software© 2000) by placing an animal's home cage inside a metal cage rack that contained photocell arrays. Basic movements were defined as movements that broke a beam in an X-Y plane. Photodetectors were connected to an IBM computer and test session data were electronically recorded. Each photocell beam interruption constituted one activity count, and total counts per 10-minute period were tabulated for a 180-minute test session. Each test session consisted of a one-hour habituation period, followed by a two-hour observation period, during which time the effect of the agents on locomotor activity was assessed. One-way measures analysis of variance (ANOVA) was conducted to determine a treatment effect. Spontaneous locomotor activity data were expressed as mean±SEM and plotted in 5-minute bins and one-way ANOVA was conducted on the first 60 minutes of each session. The level of significance was $p<0.05$.

Microdialysis. For probe implantation, each rat was given a 0.05 mL subcutaneous (s.c.) injection of Buprenex (buprenorphine hydrochloride) at 0.06 mg/kg, five minutes prior to anesthesia. Animals were anesthetized with an Isoflurane/air mixture and stereotaxically implanted with a guide cannula (Eicom) in the prefrontal cortex (incisor bar, −3.5 mm, +3.2 mm anterior, 0.8 mm lateral and 1 mm ventral to Bregma (Paxinos and Watson, 1997)). The guide cannula was secured in place with skull screws and dental cement. Probe-implanted animals were allowed at least four days to recover from surgery prior to experimentation. Dialysis experiments were conducted between 8:00 a.m. and 3:00 p.m. in a controlled environment. Animals remained in their home cage throughout each study.

Doses of SB269970, Compound A, SB269970 and citalopram, or Compound A and citalopram were given subcutaneously. All compounds were formulated in 5% Pharmasolve and 95% dextrose. Dialysis probes (4-millimeter active membrane length; Eicom) were perfused with artificial cerebral spinal fluid (147 mM NaCl, 4 mM KCl, 0.85 mM $MgCl_2$, 2.3 mM $CaCl_2$, pH 7.4) at a flow rate of 1 μL/min and implanted the afternoon prior to sample collection. Each probe was connected via FEP tubing to a liquid swivel (QM; Instech) mounted on a counter-balance arm. The following morning, two hours of baseline samples were collected into a 96-well plate (Sarstedt, 96-well multiply PCR) via a four-channel fraction collector (Eicom). Samples were collected every 30 minutes for 6 hours in the 96-well plates, which contained 7.5 μL of an antioxidant solution (0.1 M acetic acid, 1 mM oxalic acid and 3 mM L-cysteine in sterile water) maintained at 4° C. Samples were analyzed immediately following each experiment.

Dialysis samples were analyzed for 5-hydroxytryptamine (5-HT), dopamine (DA), and norepinephrine (NE) by high-performance liquid chromatography with electrochemical detection (HPLC-ECD). Separation of DA was achieved using an Eicompak PP-ODS column (4.6 mm (interior diameter)×30 mm; Eicom) with the potential of the graphite electrode set to +400 mV against a Ag/AgCl reference electrode. The mobile phase consisted of 100 mM sodium phosphate buffer (pH 6.0), 500 mg/L decanesulfonic acid, 50 mg/L EDTA, and 1% (vol/vol) methanol. NE detection was achieved by HPLC-ECD using an Eicompak CA-50DS column (2.1 mm (interior diameter)×150 mm; Eicom) with the potential of the graphite electrode (Eicom) set to +450 mV against an Ag/AgCl reference electrode. The mobile phase consisted of 100 mM sodium phosphate buffer (pH 6.0), 400 mg/L octanesulphonic acid, 50 mg/L EDTA, and 5% (vol/vol) methanol. The concentration for each sample was calculated from the peak area of the chromatographic signal and the slope from the corresponding standard curve. The percent change from baseline values was calculated from the mean basal value of each neurotransmitter for each animal, and presented as mean±SEM. The area under the curve (AUC) values were calculated by the summation of the difference between each neurotransmitter post-agent administration and the mean percent of basal release value (100%). For statistical analysis, a one-way analysis of variance (ANOVA) and Newman-Keuels multiple conversion post hoc test was performed. Data was graphed and statistics were calculated using Prism software (GraphPad, San Diego, Calif.).

Pharmacokinetics and bioanalysis. Rats received an s.c. dose of citalopram (3 mg/kg) alone, citalopram (3 mg/kg) and SB269970 (10 mg/kg), or citalopram (3 mg/kg) and Compound A (1 mg/kg). Dosing was followed by blood sampling via cardiac puncture over a time course. Brains were removed from animals and homogenized for LC/MS-MS analysis.

All blood samples were deproteinized by making 1:4 dilutions of each sample with acetonitrile (one part sample:four parts acetonitrile) and mixing vigorously. These samples were incubated for five minutes, and then centrifuged at 14,000 rpm in a microcentrifuge for four minutes. The supernatant was recovered in auto-sampler vials and diluted 1:1 with sterile water. Samples were analyzed by LC-MS/MS. A Vydac SP C18 2.1×50 mm analytical column was used for separation.

Independent Effects: 5-HT7 Receptor Antagonism by SB269970 and Compound A on Mouse Behavior in the Setting of the Tail Suspension Test The tail suspension test is a behavioral test in mice that is employed to characterize clinical efficacy of certain psychotropic agents, including antidepressants (Steru et al., *Prog. Neuropsychopharmacol. & Biol. Psychiatry*, Vol. 11(6), pp. 659-671 (1987). Animals administered an antidepressant drug and subjected to the tail suspension test typically display an increase in struggling and a decrease in the amount of time that the animal spends immobile during the test, compared to vehicle treated animals. Thus, agents may be administered to animals in the setting of the tail suspension test in order to assess their antidepressant qualities by measuring these parameters. Accordingly, either of the 5-HT7 receptor antagonists SB269970 or Compound A, either alone or together with the SSRI citalopram, was administered to independent groups of mice, and the effects on struggling time and immobilization time were measured in the setting of the tail suspension test for each group.

Figure 1B:
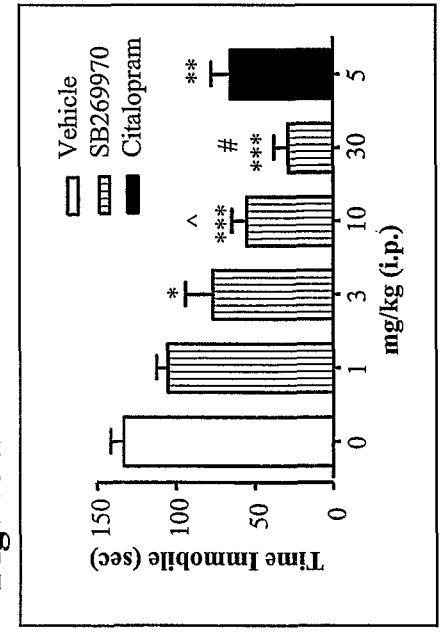

As depicted in FIG. 1A, administration of 3, 10, and 30 mg/kg of SB269970 decreased the immobility time of mice in the tail suspension test treated mice by 43%, 59% and 79%, respectively, compared to vehicle (p<0.05, p<0.001, and p<0.001, respectively). These efficacies were similar to the efficacy observed with administration of 5 mg/kg i.p. citalopram used as a positive control (immobility time decreased by 51% vs. vehicle, p<0.01). As depicted in FIG. 1B, administration of 0.3, 0.5, and 1 mg/kg of Compound A decreased the immobility time of treated mice by 31%, 39%, and 51%, respectively, compared to vehicle (p<0.05, p<0.01, and p<0.01, respectively, with greatest efficacy observed at the 1 mg/kg dose.

Collectively, these results reflect that each of the 5-HT7 receptor antagonists tested, SB269970 and Compound A, exerts an antidepressant effect on treated animals when administered alone relative to vehicle controls, and that Compound A appears to exhibit a greater potency as an antidepressant than SB269970.

Figure 2A:
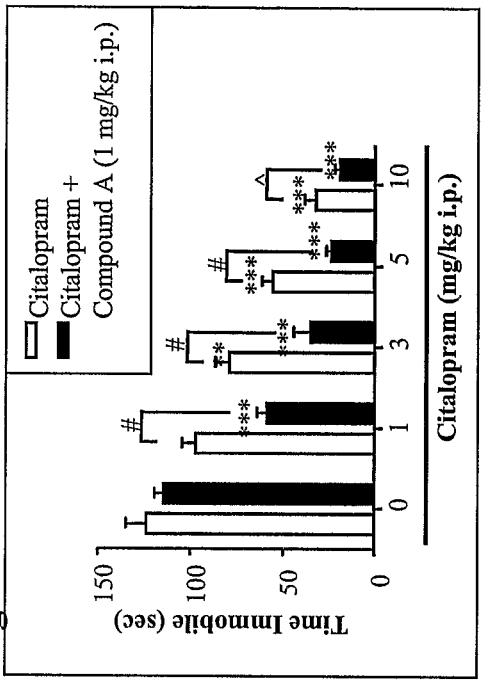
FIGS. 2A and 2B depict effects of administration of the indicated doses of the SSRI, 1-(3-dimethylaminopropyl)-1-(4-fluorophenyl)-1,3-dihydroisobenzofuran-5-carbonitrile (citalopram) alone and when co-administered independently with the indicated doses of each of the 5-HT receptor antagonists, SB269970 and Compound A, on mice in the setting of the tail suspension test (FIGS. 2A and 2B, respectively). Data bars represent the mean±SEM and n=8. =p<0.01 vs. vehicle group, *=p<0.001 vs. vehicle group, ^=p<0.05 vs. citalopram alone, and #=p<0.001 vs. citalopram alone.
Figure 2B:
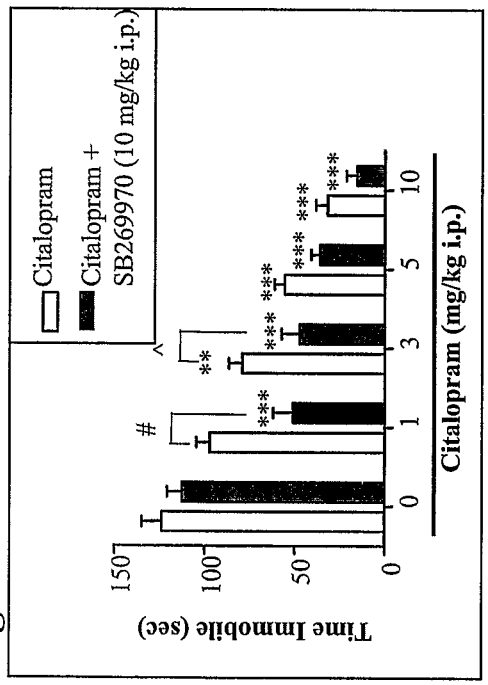

Combined Effects of 5-HT7 Receptor Antagonism and Serotonin Reuptake Inhibition by SB269970 or Compound A with Citalopram Co-Administration In an effort to investigate whether a combined effect elicited by 5-HT7 receptor antagonism and serotonin reuptake inhibition might be observed in the setting of the tail suspension test, SB269970 and Compound A were independently co-administered with citalopram in the setting of the tail suspension test. When citalopram was administered alone i.p. at doses of 3, 5 and 10 mg/kg, immobility time was significantly decreased compared to administration of vehicle alone (35%, 54%, and 74% decrease, (p<0.01, p<0.001, and p<0.001), respectively; see FIGS. 2A and 2B). Co-administration of SB269970 (10 mg/kg i.p.) and citalopram at 1, 3, 5 and 10 mg/kg i.p. each significantly decreased immobility time relative to vehicle alone by 55%, 58%, 68%, and 86%, respectively (p<0.001 for all doses; see FIG. 2A). Co-administration of 1 mg/kg and 3 mg/kg doses of citalopram with SB269970 at 10 mg/kg i.p. each significantly enhanced the effect of citalopram administration alone (55% vs. 20% (p<0.001) and 58% vs. 35% (p<0.05), respectively; see FIG. 2A). Co-administration of 1, 3, 5, and 10 mg/kg doses of citalopram with Compound A at 1 mg/kg i.p.—each a tenfold lower dosage than the respective dosage used for SB269970—each decreased immobility time relative to vehicle alone by 49%%, 70% %, 80%%, and 84%%, respectively (p<0.001 for all doses; see FIG. 2B). The effect of co-administration with Compound A was most pronounced at the 1 mg/kg, 3 mg/kg, and 5 mg/ml citalopram doses relative to the effect of citalopram administration alone (49% vs. 21% (p<0.001), 70% vs. 36% (p<0.001), and 80% vs. 54% (p<0.001), respectively; see FIG. 2B).

Figure 3A:
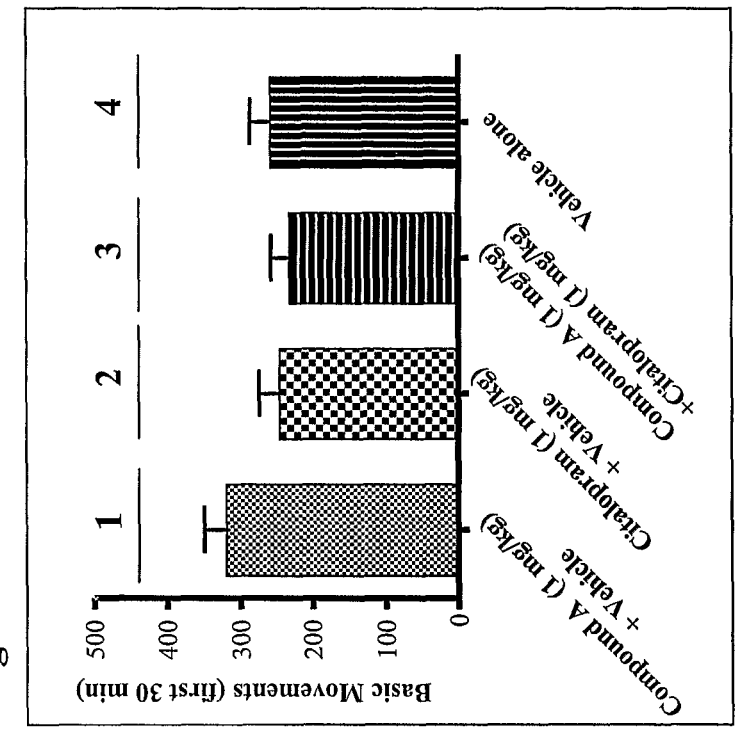
FIGS. 3A and 3B depict effects of administration of the indicated doses of citalopram alone and when co-administered with the indicated doses of each of the 5-HT receptor antagonists, SB269970 and Compound A, in the setting of the locomotor activity test. Data bars represent the mean±SEM, with n=12 and p>0.05.
Figure 3B:
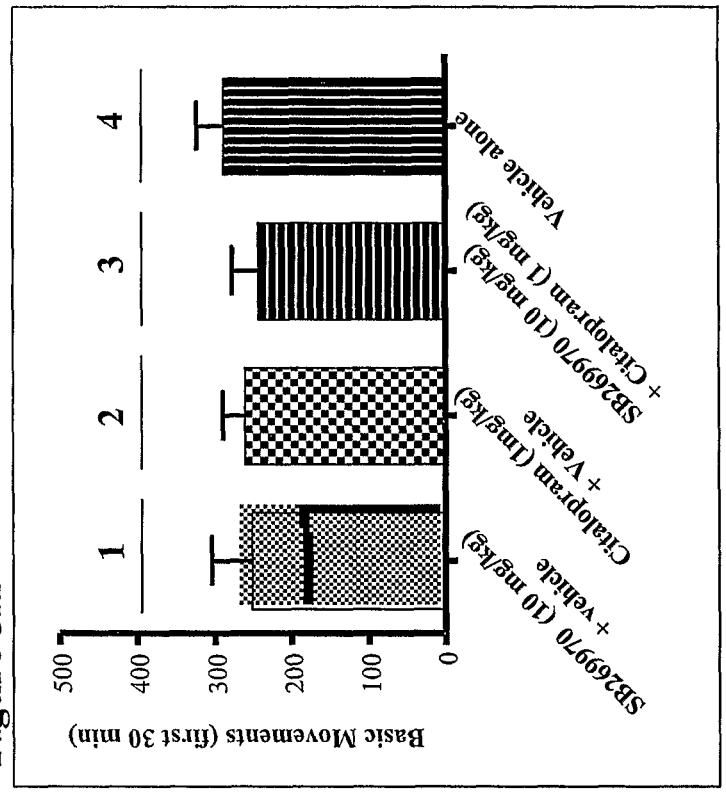

None of SB269970 (10 mg/kg i.p), Compound A (1 mg/kg i.p), or citalopram (1 mg/kg i.p.) significantly altered locomotor activity of treated mice within the first 30 minutes subsequent to administration of the compound compared to that observed in vehicle-treated mice throughout the same time period (FIGS. 3A and 3B, respectively. In each figure, compare lane 1 vs. lane 4 and lane 2 vs. lane 4, respectively (p>0.05 for all comparisons)). Similarly, neither co-administration of SB269970 (10 mg/kg i.p) nor Compound A (1 mg/kg i.p.) with citalopram (1 mg/kg i.p.) significantly altered locomotor activity of treated mice, relative to citalopram alone or to vehicle control, within the first 30 minutes subsequent to administration of the compounds (FIGS. 3A and 3B, respectively. In each figure, compare lane 3 vs. lane 2 and lane 3 vs. lane 4, respectively (p>0.05 for all comparisons)). Collectively, these results reflect that co-administration of either SB269970 or Compound A with citalopram significantly potentiates the antidepressant effects observed with citalopram in the setting of the tail suspension test. While the potentiation efficacy was found to be dose-dependent with respect to citalopram dosage in both co-administration regimens tested, Compound A was found to be roughly ten times as potent as SB269970, in that approximately one-tenth the amount of Compound A relative to the amount of SB269970 was sufficient to potentiate to a similar magnitude the effect of citalopram alone on immobility time in the setting of the tail suspension test.

Figure 4B:
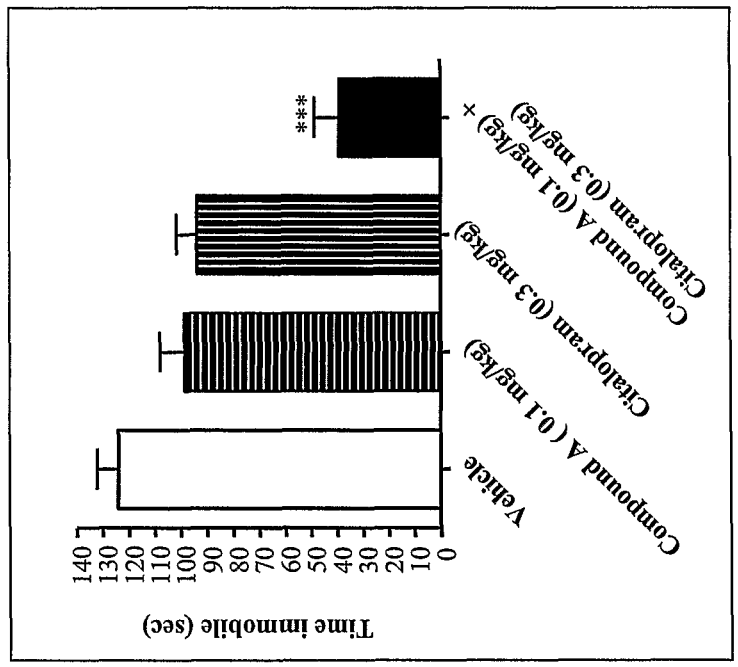
FIGS. 4A and 4B depict effects of administration of sub-efficacious doses of either SB269970 alone, Compound A alone, or citalopram alone, and of co-administration of citalopram independently with SB269970 (FIG. 4A) and Compound A (FIG. 4B). Data bars represent the mean±SEM; n=8 and ***=p<0.001 vs. vehicle group.
Figure 4A:
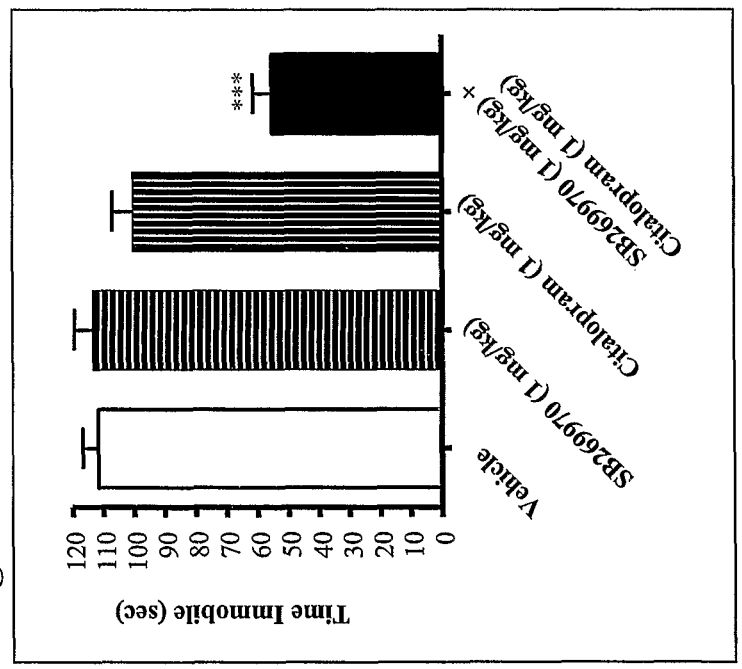

Effect of Combination of Sub-Efficacious Doses of Citalopram and Either SB269970 or Compound A The previous examples demonstrate that the co-administration of efficacious doses of a 5-HT7 receptor antagonist and an SSRI can produce a greater effect on immobility time than that observed when an efficacious dose of either substance is administered alone. In an effort to determine whether co-administration of sub-efficacious doses of a 5-HT7 receptor antagonist and an SSRI might yield an efficacious result, sub-efficacious doses of either citalopram or SB269970 were co-administered with sub-efficacious doses of citalopram to mice, who were then subjected to the tail suspension test. As reflected in FIG. 4A, neither citalopram (1 mg/kg i.p.) nor SB269970 (1 mg/kg i.p.) significantly altered immobility time compared to vehicle treated mice (p>0.05). In contrast, co-administration of these sub-efficacious doses of citalopram (1 mg/kg i.p.) and SB269970 (1 mg/kg i.p.) significantly decreased the immobility time compared to that observed with vehicle alone (p<0.001; FIG. 4A). Similarly, citalopram (1 mg/kg i.p.) and Compound A, when administered alone at sub-efficacious doses (0.3 mg/kg i.p. and 0.1 mg/kg i.p., respectively) each only modestly decreased immobility times; however, when both citalopram and Compound A were co-administered at these sub-efficacious doses, a significant decrease in immobility time was observed compared to that observed with vehicle alone (FIG. 4B).

Figure 5A:
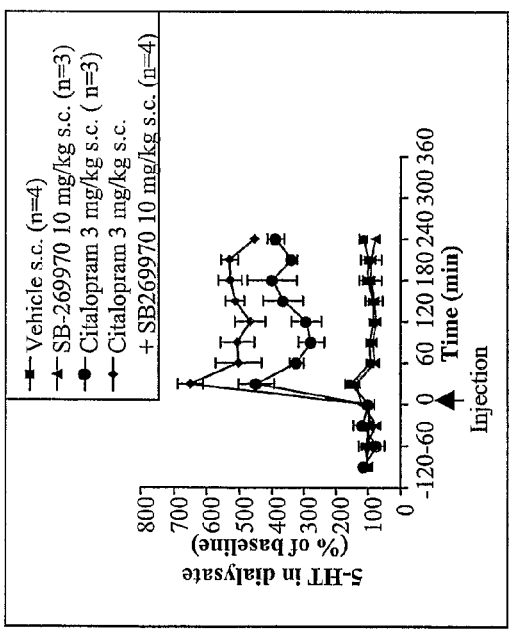
FIGS. 5A-5D depict effects on prefrontal cortical dialysate 5-HT levels from rats that were administered the indicated doses of either citalopram, SB269970, or Compound A, or co-administered the indicated doses of citalopram and SB269970 or citalopram and Compound A. All rats were administered agents after measuring stable baseline levels over 90-minute fractions, as indicated with arrow.
Figure 5B:
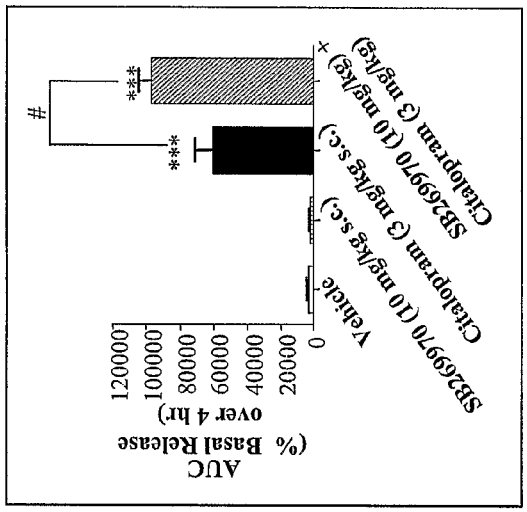
Figure 5C:
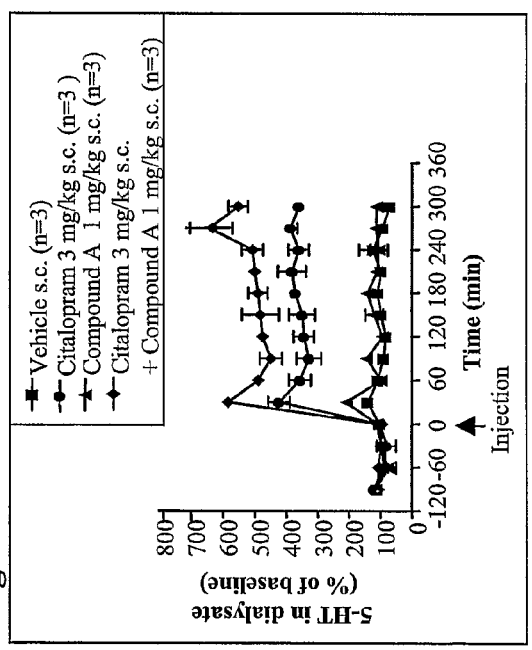
Figure 5D:
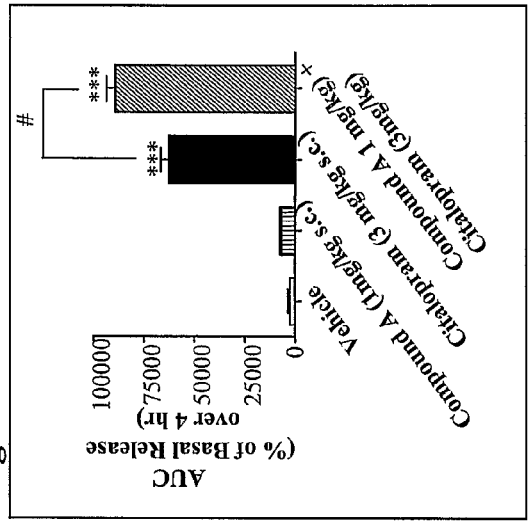

Effect of 5-HT7 Receptor Antagonism and Serotonin Reuptake Inhibition on Prefrontal Cortical Levels of 5-hydroxytryptamine In order to determine whether the potentiating effect of co-administration a 5-HT7 receptor antagonist with an SSRI might be related to an increase in extracellular cortical 5-hydroxytryptamine (5-HT) levels, in vivo microdialysis experiments were performed on mice administered either citalopram, SB269970, Compound A, or co-administered citalopram with either SB269970 or Compound A. Doses of 10 mg/kg SB269970, 1 mg/kg Compound A, and 3 mg/kg citalopram, which were each efficacious when administered alone in tail suspension tests; see e.g., FIGS. 1A-1B) were selected for initial microdialysis studies, and levels of 5-hydroxytryptamine (5-HT), dopamine (DA), and norepinephrine (NE) were followed after dosing. Basal levels of 5-HT, DA, and NE in dialysate from the frontal cortex (without adjusting for probe recovery) was 0.046±0.002 pg/10 µL (n=30), 0.12±0.008 pg/10 µL (n=30) and 0.215±0.007 pg/10 µL (n=30), respectively. Whereas neither administration of SB269970 (10 mg/kg s.c.) alone nor Compound A (1 mg/kg s.c.) alone increased extracellular 5-HT concentration compared to vehicle, administration of citalopram (3 mg/kg s.c.) alone significantly increased the extracellular concentration of 5-HT compared to vehicle (FIG. 5A and FIG. 5C, respectively), similar to previous reports (see e.g., Bymaster et al., *Psychopharmacology* (*Berl*), Vol. 160(4), pp. 353-361 (2002)). Extracelluar 5-HT concentration was significantly increased upon co-administration of either SB269970 (FIG. 5A) or Compound A (FIG. 5C) relative to 5-HT concentration observed upon citalopram administration alone. Area-under-the-curve (AUC) analysis of the data presented in FIGS. 5A and 5C further reflected the significance of the potentiating effect co-administration of citalopram and either SB269970 (FIG. 5B) or Compound A (FIG. 5D).

Figure 6A:
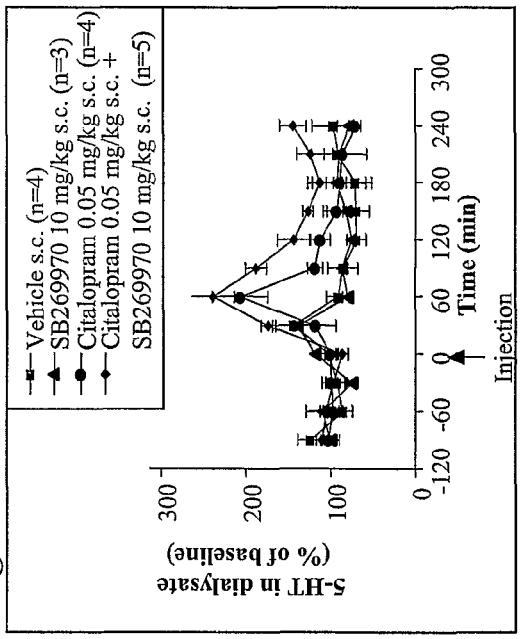
FIGS. 6A-6D depict effects on prefrontal cortical dialysate 5-HT levels from rats that were administered the indicated doses of either citalopram, SB269970, or Compound A, or co-administered the indicated doses of citalopram and SB269970 or citalopram and Compound A.
Figure 6B:
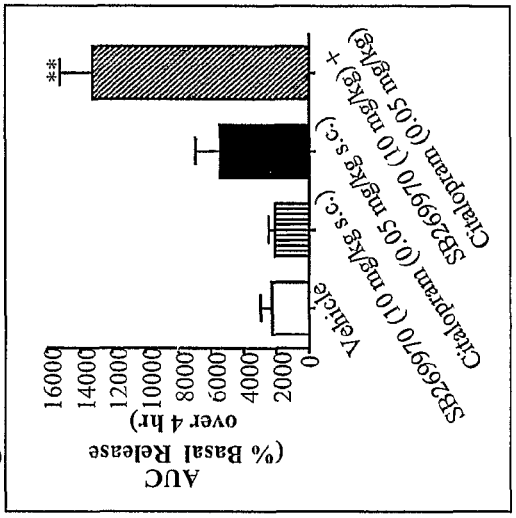
Figure 6C:
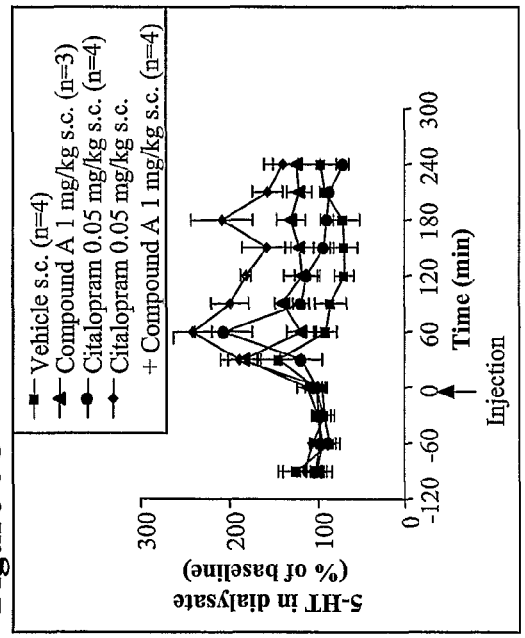
Figure 6D:
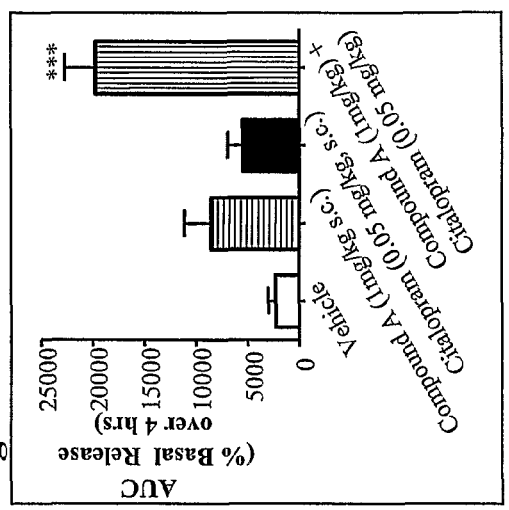

Additional experiments were performed using a sub-efficacious dose of citalopram (0.05 mg/kg s.c.), which did not significantly increase extracellular concentration of 5-HT (FIGS. 6A and 6C) in combination with either SB269970 (10 mg/kg s.c.) or Compound A (1 mg/kg s.c.). Whereas the sub-efficacious citalopram dose did not significantly increase extracellular 5-HT concentrations, co-administration of 0.05 mg/kg citalopram with either 10 mg/mL SB269970 or 1 mg/mL Compound A resulted in a significant increase in extracellular 5-HT concentration relative to 5-HT concentration observed with citalopram administration alone (FIG. 6A and FIG. 6C, respectively). AUC analysis of the data presented in FIGS. 6A and 6C further reflected the significance of the potentiating effect of co-administration of citalopram and either SB269970 (FIG. 6B) or Compound A (FIG. 6D).

None of citalopram (0.05 or 3 mg/kg s.c.), SB269970 (10 mg/kg s.c.), Compound A (1 mg/kg s.c.), co-administration of citalopram (0.05 or 3 mg/kg s.c.) and SB269970 (10 mg/kg s.c.), or co-administration of citalopram (0.05 or 3 mg/kg s.c.) and Compound A (1 mg/kg s.c.) induced significant change in extracellular concentrations of DA or NE.

Figure 7B:
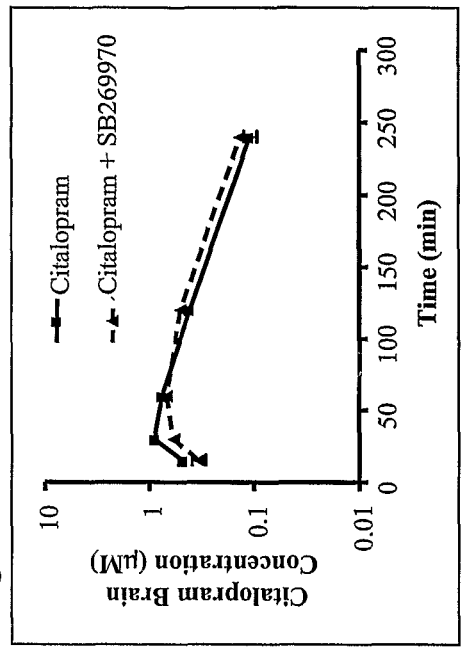
FIGS. 7A and 7B depict plasma (FIG. 7A) and brain (FIG. 7B) citalopram levels in rats after subcutaneous administration of citalopram alone (3 mg/kg) or subcutaneous co-administration of citalopram (3 mg/kg) and SB269970 (10 mg/kg). Data represents mean±SEM; n=3.
Figure 7A:
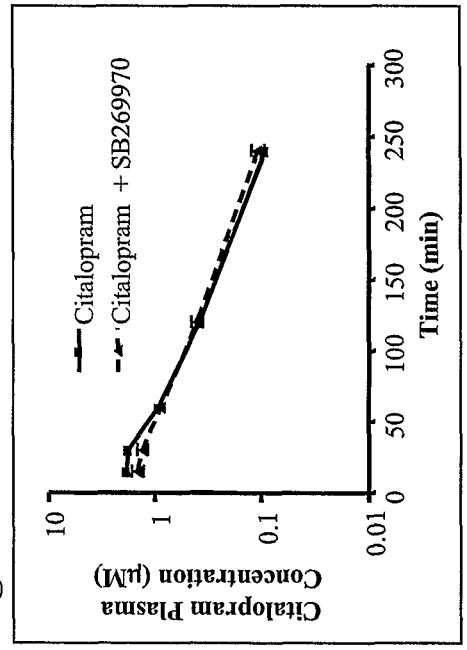

Effect of SB269970 on Citalopram Blood Brain Barrier Penetration and Pharmacokinetics Parameters Citalopram plasma and brain concentrations were determined following s.c. dosing of citalopram alone (3 mg/kg) or co-administration of citalopram (3 mg/kg) and SB269970 (10 mg/kg). Co-administration of SB269970 did not affect citalopram plasma or brain concentration, as reflected in FIGS. 7A and 7B, respectively.

Analysis of Sleep/Wake States in Rats Following the Co-Administration of Citalopram and the 5-HT$_7$ Antagonist Compound A or SB269970

The response to administration of the selective serotonin reuptake inhibitor citalopram in combination with the Compound A or SB269970 on sleep/wake states was analyzed using a rat telemetric in vivo system. For the determination of EEG/EMG waveforms, two stainless steel screw electrodes for electroencephalogram (EEG) (frontal and parietal cortex) and wire electrodes electromyogram (EMG) (dorsal neck muscles) were implanted in each animal under isofluorane anesthesia. Electrodes were connected to a sterile 2-channel telemetric device (Data Sciences TL10M3-F50-EET) that had been implanted in the intraperitoneal cavity. The animals were allowed to recover for two weeks following surgery and then moved to their designated housing/procedure room to allow for adaptation to the recording chamber and environment. On the designated day the animals were to receive vehicle or compound administration, telemetric devices were activated in each animal ten minutes before injection. EEG/EMG traces were recorded on an IBM PC-compatible computer using Dataquest A.R.T software (Data Sciences, Inc.) at a sampling rate of 100 Hz.

At two hours after light onset (during the rodent sleep period), male Sprague-Dawley rats (n=9) were initially dosed subcutaneously with vehicle or Compound A at 0.3 mg/kg or SB269970 at 10 mg/kg. Upon completion of this first dose, animals were dosed with either citalopram (1 mg/kg) or vehicle. EEG/EMG signals were recorded for ten hours following administration of the test reagents and vigilant state (wake, NREM, or REM) was assigned in 10-second epochs by visual inspection. Quantitative analysis of EEG activity was performed by spectral analysis using Fast Fourier Transformation. Utilizing the computer program SleepSign (Kissei, Inc.), consecutive EEG/EMG recordings were divided into 10-second epochs. Vigilance states were visually assigned to these individual epochs using the conventional criteria for wake (less regular low amplitude EEG, EMG activation); non-rapid eye movement (NREM) sleep (high-amplitude EEG waves with predominant frequency in the delta range (0.5-5 Hz) and lack of body movement; rapid eye movement (REM) sleep (stable low amplitude EEG, dominance of theta activity (5.1-8 Hz frequency range), with general EMG atonia). For the quantitative analysis of the EEG signal, power spectra were calculated for each scored 10-second epoch, which was divided into five 2-second intervals and then subjected to a fast Fourier transformation (FFT) for the frequency range of 0.5-30.0 Hz. Those epochs that contained EEG artifacts were excluded from the FFT analyses. The resulting power density spectra were divided into five predetermined frequency bands: delta (0.5-5 Hz), theta (5.1-8 Hz), alpha (8.1-12 Hz), sigma (12.1-14 Hz), and beta (14.1-30 Hz). Subsequently, power spectra were averaged over all the epochs in each frequency band separately. After scoring the EEG/EMG traces, analysis and compilation of the raw data files was executed by a proprietary sleep analysis program. Using a fully customizable computer script in conjunction with the software program R, several parameters relating to the architecture (time spent in wake, NREM, or REM), continuity and consolidation of the sleep/wake cycle (i.e., bout analysis) were evaluated. A bout was defined as at least two consecutive epochs, 20 s, of wake, NREM, or REM. Micro-arousals from sleep (NREM or REM sleep bout interrupted by a 10-s epoch of wake) and awakenings from NREM (number of transitions between a NREM bout to a bout of wake) were also measured. Spectral analysis of the EEG was performed in the states of wake, NREM, and REM sleep, respectively. Results were averaged and expressed as mean±S.E.M. in defined time intervals. To determine if differences were significant at a given interval, either a one-way ANOVA with Neuman-Keuls post hoc analysis or two-way repeated measures ANOVA followed by a Bonferroni post hoc test was executed. Differences were determined to be significant if p<0.05. The results are summarized in Tables 1 and 2 below.

TABLE 1

NREM and REM sleep latencies following co-administration of citalopram (1 mg/kg) and Compound A (0.3 mg/kg) (A) or SB269970 (B) (10 mg/kg) (n = 9.)

A)

|  | Vehicle + Vehicle | Compound A + Vehicle | Vehicle + Citalopram | Compound A + Citalopram |
|---|---|---|---|---|
| NREM | 28.9 ± 3.5 | 23.0 ± 3.0 | 30.9 ± 3.8 | 28.9 ± 1.7 |
| REM | 55.4 ± 5.8 | 67.1 ± 4.2[#] | 94.3 ± 11.1* | 153.9 ± 13.2*** |

*P < 0.05 v. Vehicle + Vehicle
***P < 0.001 v. Vehicle + Vehicle, Compound A + Vehicle, and Vehicle + Citalopram
[#]P < 0.05 v. Vehicle + Citalopram

B)

|  | Vehicle + Vehicle | SB269970 + Vehicle | Vehicle + Citalopram | SB269970 + Citalopram |
|---|---|---|---|---|
| NREM | 28.9 ± 3.5 | 34.5 ± 4.2 | 30.9 ± 3.8 | 33.0 ± 4.6 |
| REM | 55.4 ± 5.8 | 78.7 ± 8.0 | 94.3 ± 11.1* | 158.7 ± 12.3** |

*P < 0.05 v. Vehicle + Vehicle
**P < 0.001 v. Vehicle + Vehicle, SB269970 + Vehicle, and Vehicle + Citalopram

TABLE 2

REM bout analysis following co-administration of citalopram (1 mg/kg) and Compound A (0.3 mg/kg) (A) or SB269970 (B) (10 mg/kg) (n = 9)

A)

|  | Vehicle + Vehicle | Compound A + Vehicle | Vehicle + Citalopram | Compound A + Citalopram |
|---|---|---|---|---|
| Number of REM Bouts | 37.8 ± 2.4 | 34.3 ± 1.4 | 35.1 ± 2.7 | 24.9 ± 1.5*** |
| REM Bout Duration (Minutes) | 1.8 ± 0.1 | 1.8 ± 0.1 | 1.7 ± 0.1 | 2.0 ± 0.1* |

*$P < 0.05$ v. Vehicle + Citalopram
***$P < 0.001$ v. Vehicle + Vehicle, Compound A + Vehicle, and Vehicle + Citalopram

B)

|  | Vehicle + Vehicle | SB269970 + Vehicle | Vehicle + Citalopram | SB269970 + Citalopram |
|---|---|---|---|---|
| Number of REM Bouts | 37.8 ± 2.4 | 29.0 ± 1.5*, ** | 35.1 ± 2.7 | 23.0 ± 1.3*** |
| REM Bout Duration (Minutes) | 1.8 ± 0.1 | 2.0 ± 0.1 | 1.7 ± 0.1 | 2.1 ± 0.1* |

Figure 8A:
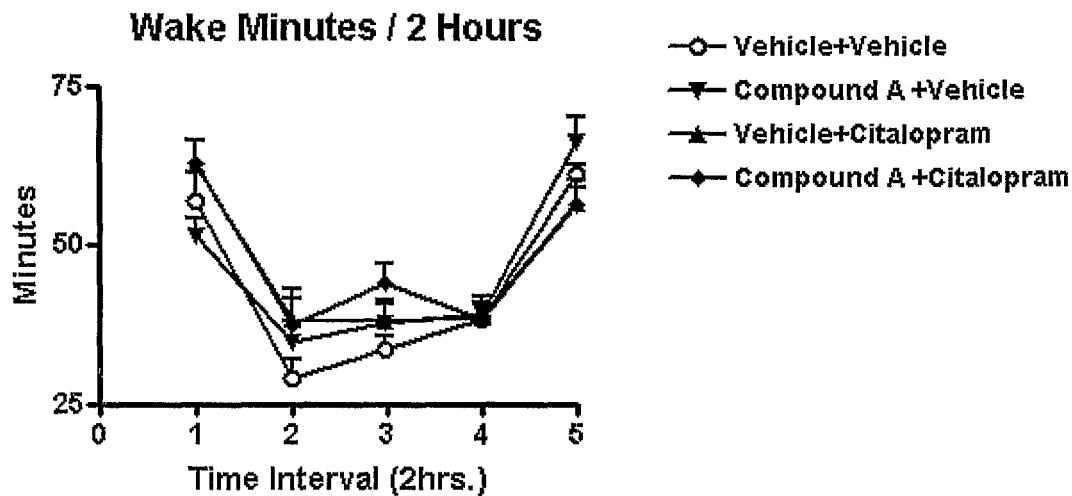
FIGS. 8A and 8B illustrates the duration of time spent awake following the co-administration of citalopram (1 mg/kg) and Compound A (0.3 mg/kg) (A) or SB269970 (B) (10 mg/kg) (n=9, average±S.E.M.).
Figure 8A:
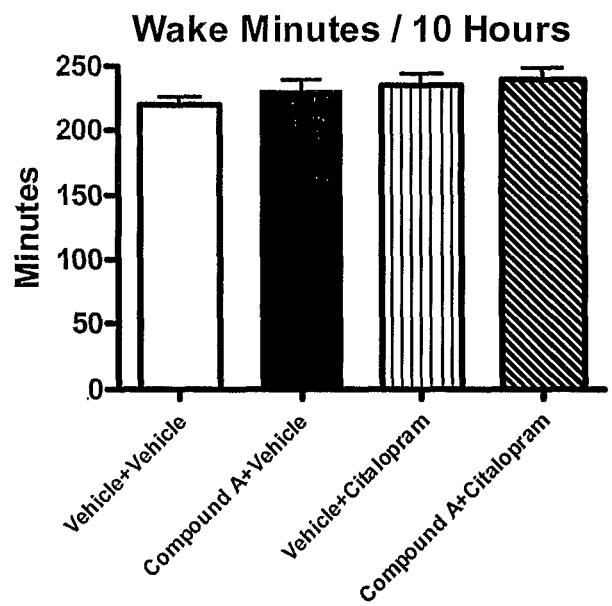
Figure 8B:
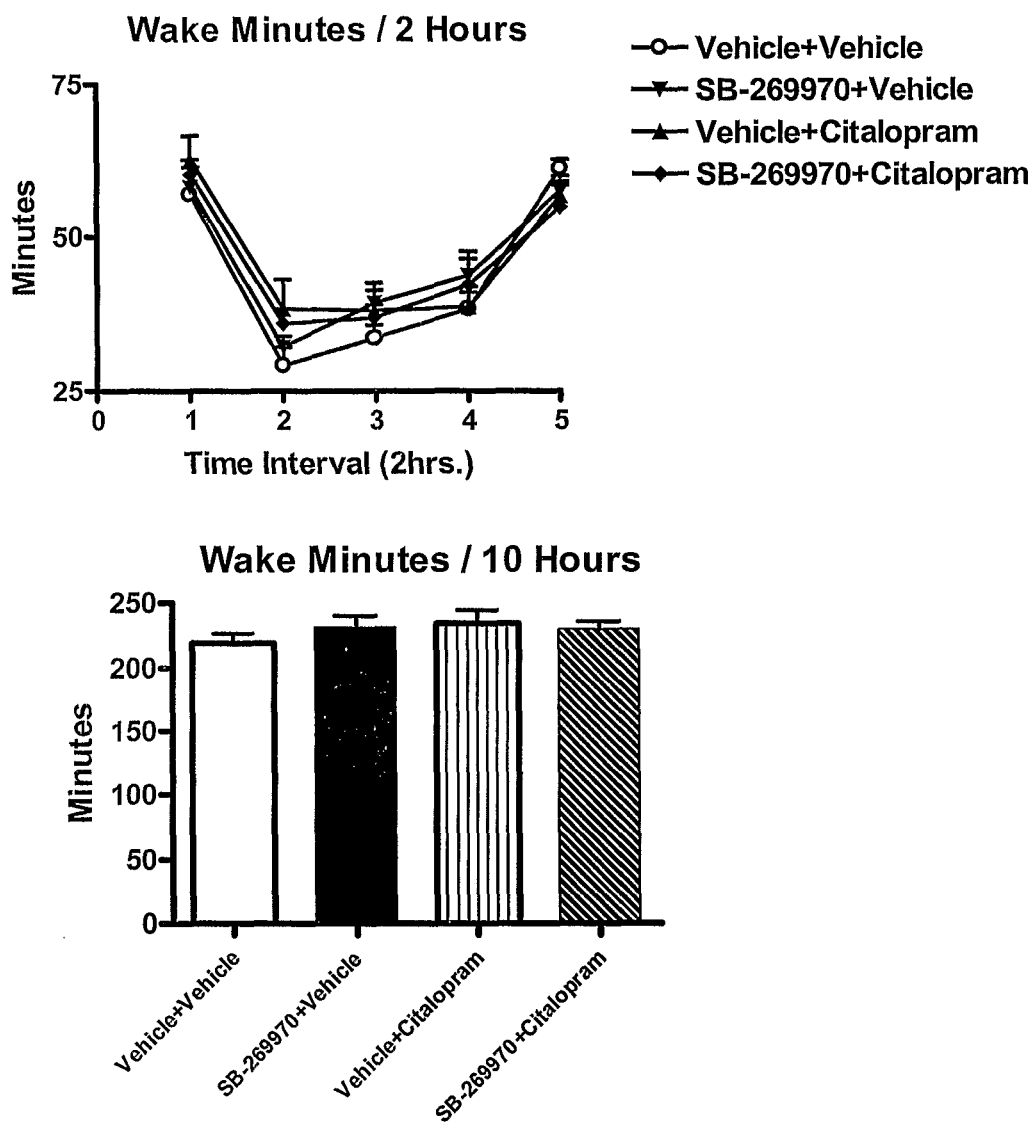
Figure 9A:
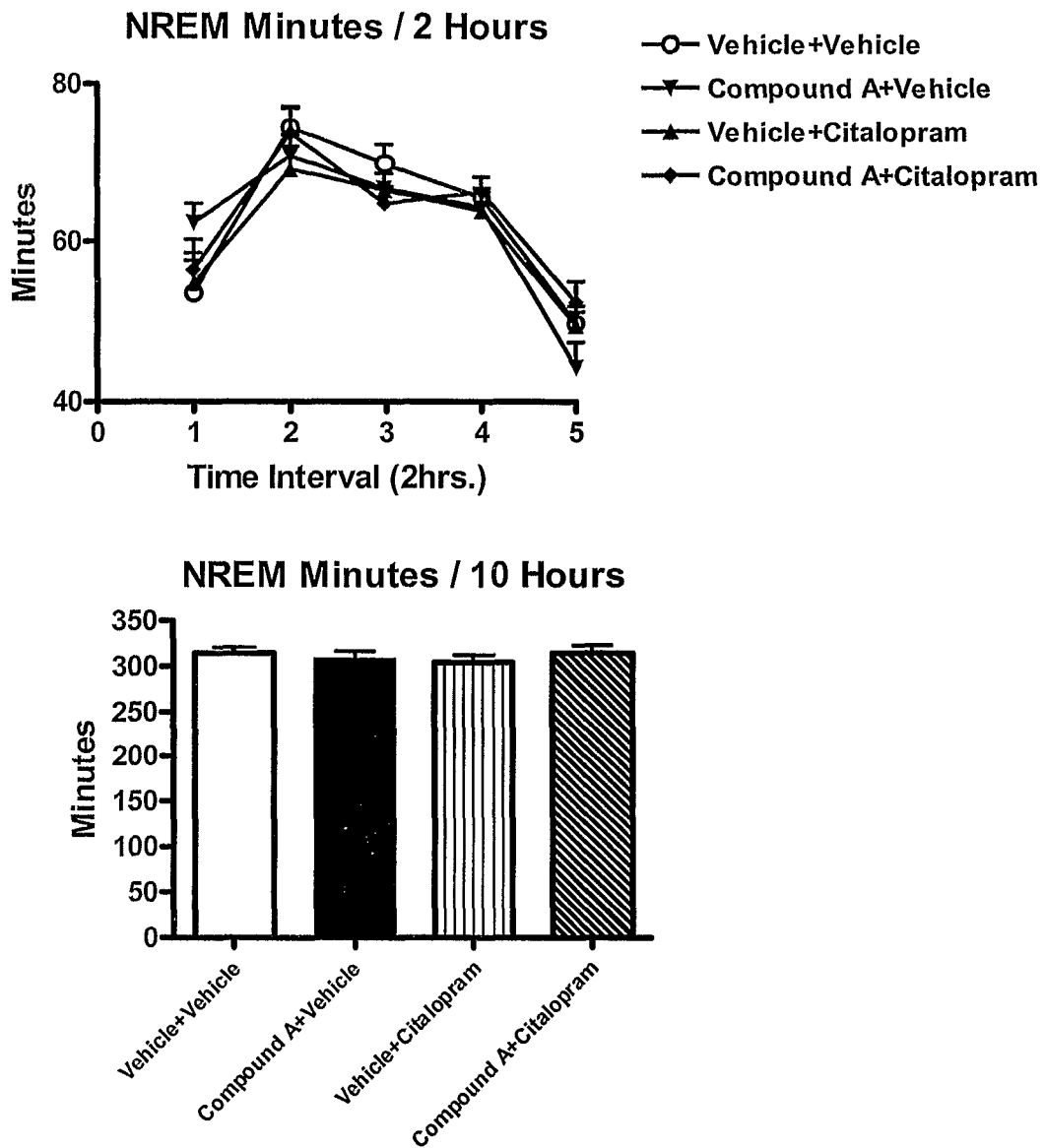
FIGS. 9A and 9B depict duration of NREM sleep following the co-administration of citalopram (1 mg/kg) and Compound A (0.3 mg/kg) (A) or SB269970 (B) (10 mg/kg) (n=9, average±S.E.M.).
Figure 9B:
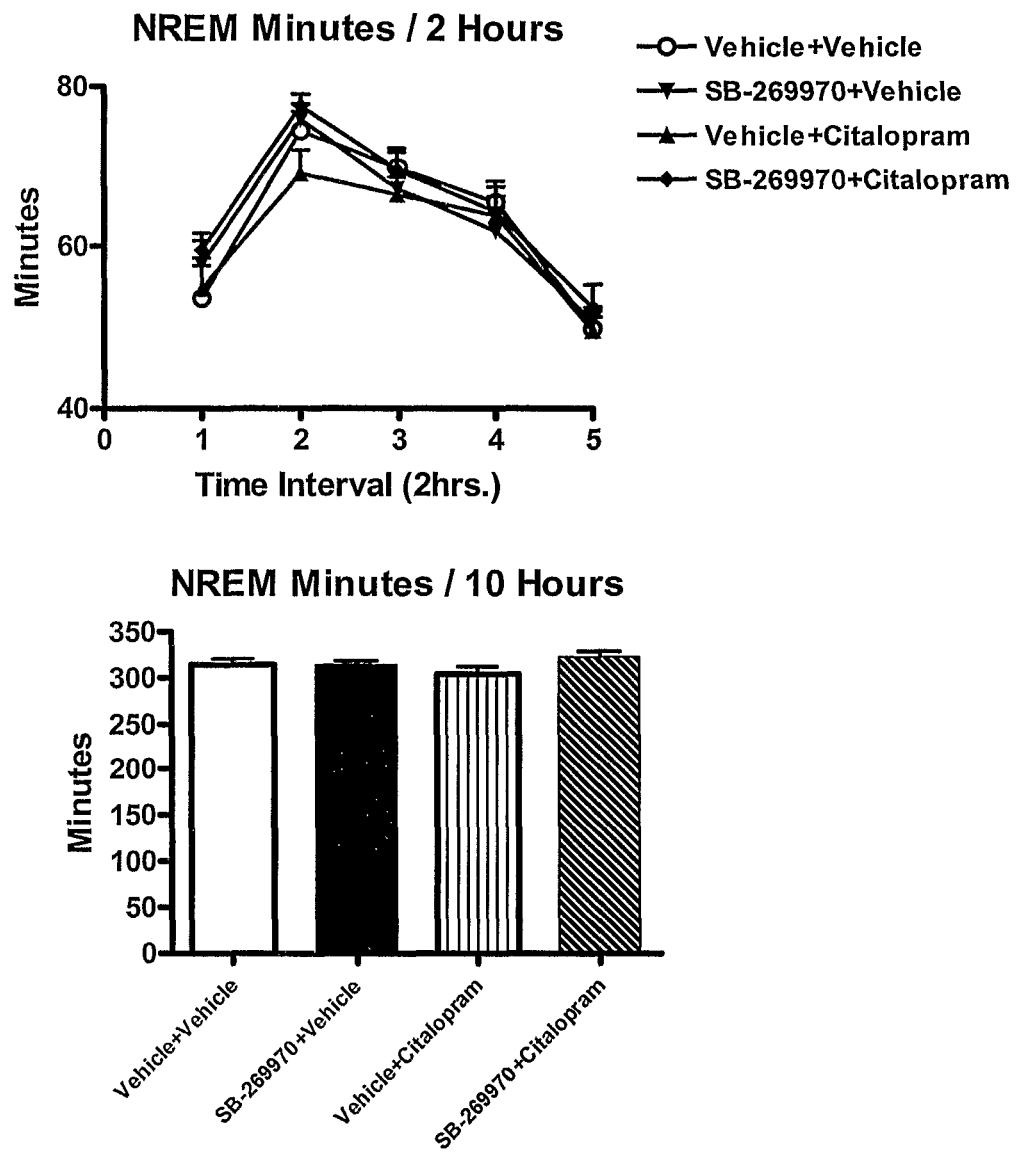
Figure 10A:
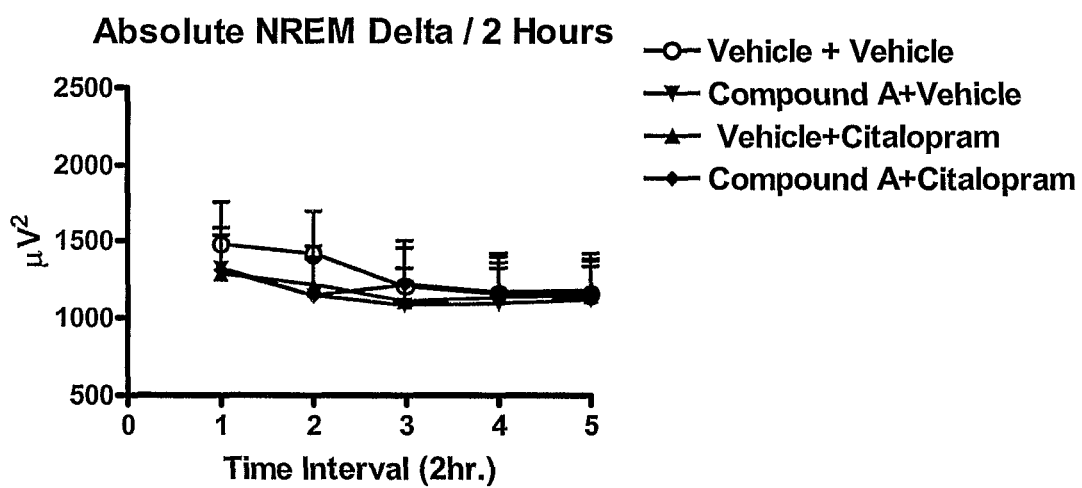
FIGS. 10A and 10B illustrate absolute NREM delta power following the co-administration of citalopram (1 mg/kg) and Compound A (0.3 mg/kg) (A) or SB269970 (B) (10 mg/kg) (n=9, average±S.E.M.).
Figure 10B:
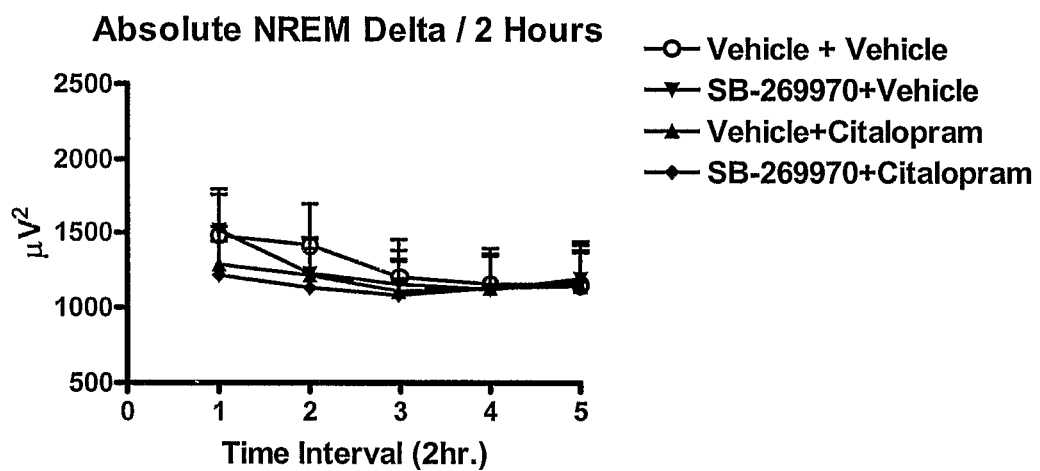
Figure 11A:
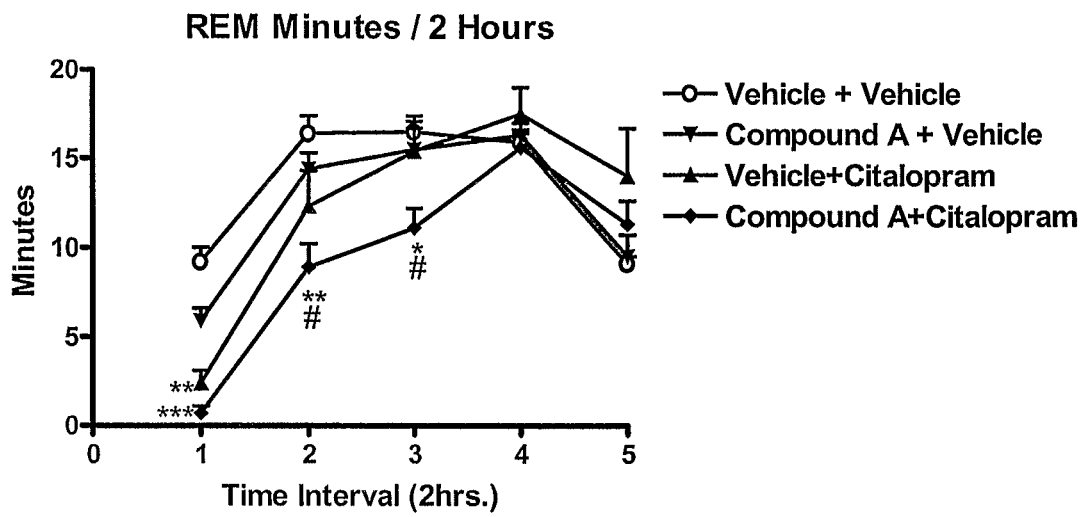
FIGS. 11A and 11B show REM sleep following the co-administration of citalopram (1 mg/kg) and Compound A (0.3 mg/kg) (A) or SB269970 (B) (10 mg/kg) (n=9, average±S.E.M.).
Figure 11A:
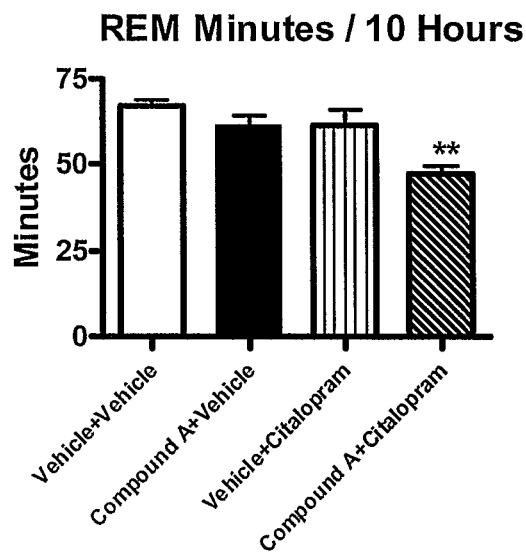
Figure 11B:
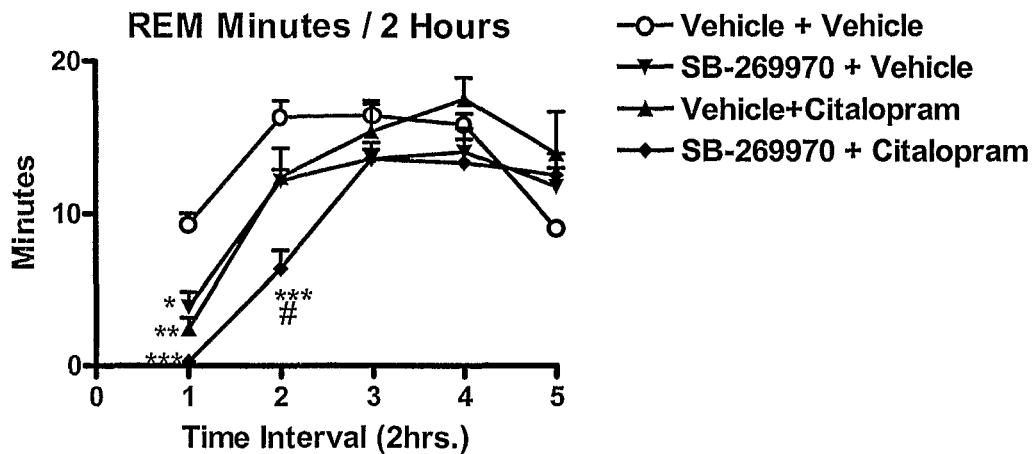
Figure 11B:
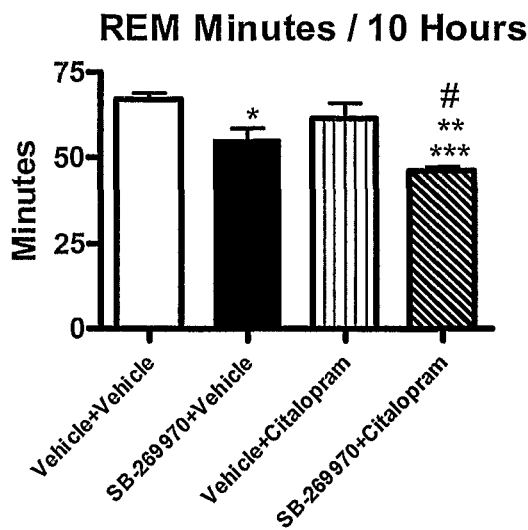
Figure 12A:
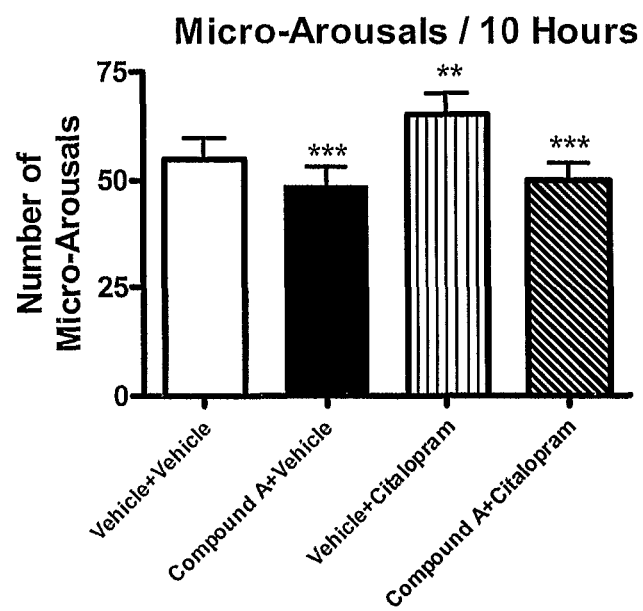
FIGS. 12A and 12B illustrate the number of micro-arousals following the co-administration of citalopram (1 mg/kg) and Compound A (0.3 mg/kg) (A) or SB269970 (B) (10 mg/kg) (n=9, average±S.E.M.).
Figure 12B:
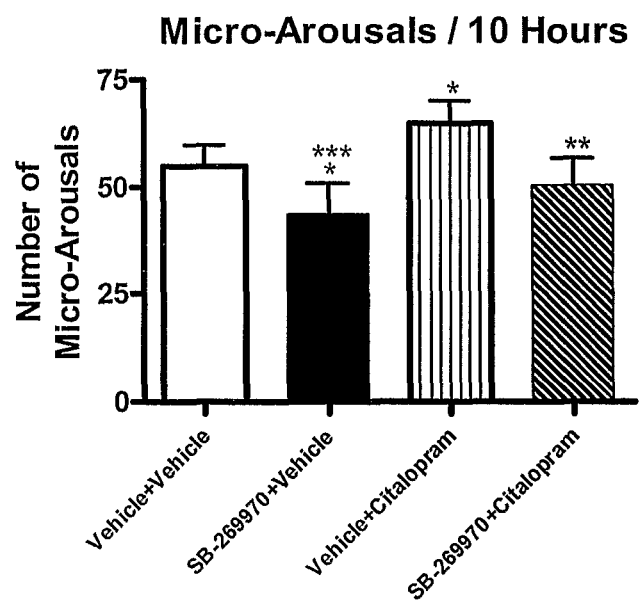

*$P < 0.05$ v. SB269970 + Citalopram
**$P < 0.01$ v. Vehicle + Vehicle and Vehicle + Citalopram
***$P < 0.001$ v. Vehicle + Vehicle and Vehicle + Citalopram Administration of citalopram, Compound A, or SB269970, either as stand-alone therapy or as a combination, did not influence the time spent awake (FIG. 8), the latency to NREM sleep (Table 1) or duration of NREM sleep (FIG. 9), or the intensity of NREM sleep as indexed by the EEG spectral analysis in the delta frequency band (FIG. 10). Citalopram treatment induced a significant increase in REM sleep latency, whereas the 5-HT7 antagonists had no effect at the doses tested (Table 1). The combination of citalopram with Compound A or SB269970 significantly delayed the onset of the first episode of REM sleep (~60 and 65 minutes, respectively) as compared to citalopram alone (Table 1). In addition, the treatment with Compound A or SB269970 potentiated the decrease in REM sleep duration induced by citalopram (FIG. 11). This inhibitory effect on REM sleep duration was mainly due to a decrease in the number of REM sleep bouts whereas the mean duration was slightly increased (Table 2). Interestingly, the administration of these two 5-HT7 antagonists in combination with citalopram resulted in decreased sleep fragmentation as evidenced by a significant decrease in the number of micro-arousals (FIG. 12).

While the invention has been illustrated by reference to examples and preferred embodiments, it is understood that the invention is intended to be not limited by the foregoing detailed description, but defined by the appended claims applying principles of patent law.

What is claimed is:

1. A pharmaceutical composition comprising:
    (a) (i) a therapeutically effective amount of a 5-HT7 receptor antagonist, wherein said 5-HT7 receptor antagonist is selected from the group consisting of:
    (R)-3-[2-[2-(4-Methylpiperidin-1-yl)ethyl]pyrrolidine-1-sulfonyl]phenol;
    (R)-3,N-Dimethyl-N-[1-methyl-3-(4-methylpiperidin-1-yl)propyl]benzene sulfonamide;
    R-(+)-1-(toluene-3-sulfonyl)-2[2-(4-methylpiperidin-1-yl)ethyl]-pyrrolidine;
    LY-215840;
    2a-[4-4-phenyl-1,2,3,6-tetrahydropyridyl])-2a,3,4,5-tetrahydrobenzo[ed]-indol[(iH)-1;
    Ensaculin;
    S 23751;
    Zopetine;
    SB248709;
    BTS 79018; and
    1-Benzyl-3-(4-chloro-phenyl)-1,4,5,6,7,8-hexahydro-1,2,6-triaza-azulene;
    and (ii) a therapeutically effective amount of a serotonin reuptake inhibitor, said amounts together providing an effective combined amount; and
    (b) a pharmaceutically acceptable excipient.

2. A pharmaceutical composition according to claim 1, wherein the amount of said 5-HT7 receptor antagonist is a complementary amount.

3. A pharmaceutical composition according to claim 1, wherein the amount of said serotonin reuptake inhibitor is a complementary amount.

4. A pharmaceutical composition according to claim 1, wherein said serotonin reuptake inhibitor is dapoxetine, citalopram, escitalopram, fluoxetine, fluvoxamine, sertraline, paroxetine, venlafaxine, vilazodone, duloxetine, nefazodone, imipramine, femoxetine, clomipramine, cericlamine, clovoxamine, cyanodothiepin, ifoxetine, indalpine, indeloxazine, litoxetine, milnacipran, tametraline, viqualine, or zimeldine, or a pharmaceutically acceptable salt thereof.

5. A pharmaceutical composition according to claim 1, wherein said serotonin reuptake inhibitor is citalopram, sertraline, paroxetine, fluoxetine, or dapoxetine.

6. A pharmaceutical composition according to claim 1, wherein said 5-HT7 receptor antagonist is 1-Benzyl-3-(4-chloro-phenyl)-1,4,5,6,7,8-hexahydro-1,2,6-triaza-azulene and said serotonin reuptake inhibitor is citalopram.

7. A method of treating a subject suffering from or diagnosed with a serotonin-mediated disease or condition, comprising administering to a subject in need of such treatment: a therapeutically effective amount of a 5-HT7 receptor antagonist, wherein said 5-HT7 receptor antagonist is selected from the group consisting of:
    (R)-3-[2-[2-(4-Methylpiperidin-1-yl)ethyl]pyrrolidine-1-sulfonyl]phenol;
    (R)-3,N-Dimethyl-N-[1-methyl-3-(4-methylpiperidin-1-yl)propyl]benzene sulfonamide;
    R-(+)-1-(toluene-3-sulfonyl)-2-[2-(4-methylpiperidin-1-yl)ethyl]-pyrrolidine;
    LY-215840;
    2a-[4-4-phenyl-1,2,3,6-tetrahydropyridyl])-2a,3,4,5-tetrahydrobenzo[ed]-indol[(iH)-1;
    Ensaculin;
    S 23751;
    Zopetine;
    SB248709;
    BTS 79018; and
    1-Benzyl-3-(4-chloro-phenyl)-1,4,5,6,7,8-hexahydro-1,2,6-triaza-azulene;
    and a therapeutically effective amount of a serotonin reuptake inhibitor, said amounts together providing an effective combined amount.

8. A method according to claim 7, wherein the amount of said 5-HT7 receptor antagonist is a complementary amount.

9. A method according to claim 7, wherein the amount of said serotonin reuptake inhibitor is a complementary amount.

10. A method according to claim 7, wherein:

said serotonin reuptake inhibitor is a selective serotonin reuptake inhibitor;

the amount of said 5-HT7 receptor antagonist is an ameliorative amount;

and said 5-HT7 receptor antagonist is selected from the group consisting of:

(R)-3-[2-[2-(4-Methylpiperidin-1-yl)ethyl]pyrrolidine-1-sulfonyl]phenol;

(R)-3,N-Dimethyl-N-[1-methyl-3-(4-methylpiperidin-1-yl)propyl]benzene sulfonamide;

R-(+)-1-(toluene-3-sulfonyl)-2-[2-(4-methylpiperidin-1-yl)ethyl]-pyrrolidine;

LY-215840;

2a-[4-4-phenyl-1,2,3,6-tetrahydropyridyl])-2a,3,4,5-tetrahydrobenzo[ed]-indol[(iH)-1;

Ensaculin;

S 23751;

Zopetine;

SB248709;

BTS 79018; and

1-Benzyl-3-(4-chloro-phenyl)-1,4,5,6,7,8-hexahydro-1,2,6-triaza-azulene;

and pharmaceutically acceptable salts thereof.

11. The method according to claim 7, wherein the disease or condition is selected from the group consisting of depression, anxiety, sleep or wake disturbances, and jet-lag.

12. A method according to claim 7, wherein said disease or condition is depression or anxiety.

13. A method according to claim 7, wherein said selective serotonin reuptake inhibitor is citalopram.

14. A method according to claim 13, wherein said disease or condition is selected from the group consisting of depression, anxiety, sleep or wake disturbances, and jet-lag.

15. A method according to claim 13, wherein said 5-HT7 receptor antagonist is 1-Benzyl-3-(4-chloro-phenyl)-1,4,5,6,7,8-hexahydro-1,2,6-triaza-azulene.

* * * * *